(12) United States Patent
Virgin

(10) Patent No.: US 7,455,972 B2
(45) Date of Patent: Nov. 25, 2008

(54) PCR-BASED METHOD OF DETECTING MURINE CALICIVIRUS

(75) Inventor: Herbert W. Virgin, Clayton, MO (US)

(73) Assignee: Washington University, St. Louis, MO (US)

( * ) Notice: Subject to any disclaimer, the term of this patent is extended or adjusted under 35 U.S.C. 154(b) by 243 days.

(21) Appl. No.: 11/368,804

(22) Filed: Mar. 6, 2006

(65) Prior Publication Data

US 2006/0172287 A1    Aug. 3, 2006

Related U.S. Application Data

(62) Division of application No. 10/757,832, filed on Jan. 14, 2004, now Pat. No. 7,041,444.

(60) Provisional application No. 60/440,016, filed on Jan. 14, 2003.

(51) Int. Cl.
*C12Q 1/68* (2006.01)
*A61K 39/125* (2006.01)
*C07H 21/04* (2006.01)

(52) U.S. Cl. ............ 435/6; 536/23.72; 424/216.1

(58) Field of Classification Search ............ None
See application file for complete search history.

(56) References Cited

U.S. PATENT DOCUMENTS

2005/0037016 A1* 2/2005 Virgin .................. 424/186.1

OTHER PUBLICATIONS

Ratcliff et al. Journal of Clinical Microbiology, 2002, 40(11):4091-4099.*
Ball et al., "Oral Immunization with Recombinant Norwalk Virus-Like Particles Induces a Systemic and Mucosal Immune Response in Mice," J. Virol., 1998, pp. 1345-1353, vol. 72.
Geissler et al., "Feline Calicivirus Capsid Protein Expression and Capsid Assembly in Cultured Feline Cells," J. Virol., 1999, pp. 834-838, vol. 73.
Green et al., "Comparison of the Reactivities of Baculovirus-Expressed Recombinant Norwalk Virus Capsid Antigen with Those of the Native Norwalk Virus Antigen in Serologic Assays and Some Epidemiologic Observations," J. Clin. Microbiol., 1993, pp. 2185-2191, vol. 31.
Green et al., "Expression and Self-Assembly of Recombinant Capsid Protein from the Antigenically Distinct Hawaii Human Calivirus," J. Clin. Microbiol., 1997, pp. 1909-1914, vol. 35.
Guerrero et al., "Recombinant Norwalk Virus-Like Particles Administered Intranasally to Mice Induce Systemic and Mucosal (Fecal and Vaginal) Immune Responses," J. Virol., 2001, pp. 9713-9722, vol. 75.
Jiang et al., "Baculovirus Expression and Antigenic Characterization of the Capsid Proteins of Three Norwalk-Like Virus," Archives of Virol., 2002, pp. 119-130, vol. 147.
Jiang et al., "Expression, Self-Assembly, and Antigenicity of the Norwalk Virus Capsid Protein," J. Virol., 1992, pp. 6527-5532, vol. 66.
Karst et al., "STAT1-Dependent Innate Immunity to a Norwalk-Like Virus," Science, 2003, pp. 1575-1578, vol. 299.
Liang et al., "Protection Against Fatal Sindbis Virus Encephalitis by Beclin, a Novel Bct-2-Interacting Protein," J. Virol., 1998, pp. 8586-8696, vol. 72.
Pelosi et al., "The Seroepidemiology of Genogroup 1 and Genogroup 2 Norwalk-Like Viruses in Italy," J. Med. Virol., 1999, pp. 93-99, vol. 58.
Prasad et al., "Structural Studies of Recombinant Norwalk Capsids," J. Infect. Dis., 2000, pp. S317-S321, vol. 181.
White et al., "Attachment and Entry of Recombinant Norwalk Virus Capsids to Cultured Human and Animal Cell Lines," J. Virol., 1996, pp. 6589-6597, vol. 70.

* cited by examiner

*Primary Examiner*—Stacy B Chen
(74) *Attorney, Agent, or Firm*—Sonnenschein, Nath & Rosenthal LLP

(57) ABSTRACT

The invention disclosed herein relates to a newly discovered murine *norovirus,* and compositions and methods related thereto.

9 Claims, 11 Drawing Sheets

A

| | mouse strain | dead/total |
|---|---|---|
| Passage 0 | RAG/STAT-/- | 5/6 |
| Passage 1 | RAG/STAT-/- | 15/15 |
| Passage 2 | IFNαβγR-/- | 15/15 |
| | IFNαβγR-/- (filtered) | 9/13 |
| | 129 | 0/4 | mock

MNV-1

MNV-1

MNV-1

Discovery and sequencing of new virus genome

A Norwalk virus genome (7654 bp) as a framework

B MNV-1 genome (7726 bp)

A Western blot analysis of capsid protein expression

— 75kDa
— 50kDa
— 37kDa recombinant baculovirus | neg. control negative stain EM of MNV-1 VLPs

B Baculovirus LacZ (negative control)

C VLPs in infected cell supernatants

D purified VLPs

Figure 6

Tissue MCV1 RNA levels after infection via different routes

Figure 8

Spleen sections of STAT1-/- 3dpi after p.o. inoculation with MNV-1

Figure 9

PCR-BASED METHOD OF DETECTING MURINE CALICIVIRUS

CROSS REFERENCE TO RELATED APPLICATIONS

This application is a divisional of U.S. patent application Ser. No. 10/757,832, entitled, "Murine Calicivirus" filed Jan. 14, 2004, now U.S. Pat. No. 7,041,444, which claims the benefit of priority to Provisional U.S. Patent Application Ser. No. 60/440,016, filed Jan. 14, 2003, which applications are hereby incorporated herein by reference in their respective entireties.

REFERENCE TO GOVERNMENT GRANT

This invention was made with government support under Grant No. RO1 A149286. The United States government may have certain rights in the invention.

BACKGROUND

The Caliciviridae are a family of positive-sense, single-stranded RNA viruses with a 7-8 kb genome that are divided into 4 distinct genera and further subdivided into genogroups. The genera Norwalk-like viruses, together with the closely related Sapporo-like viruses, recently renamed *Noroviruses* and *Sapoviruses* (Mayo, M. A., *Arch. Virol.* 147:1655-1656, 2002), make up human caliciviruses (Kapikian, A. Z. et al., *J. Virol.* 10:1075-1081, 1972; Jiang, X. et al., *Science* 250:1580-1583, 1990; Jiang, X. et al., *Virol.* 195:51-61, 1993; Hardy, M. E. et al., *Virus Genes* 12:287-290, 1996). *Noroviruses* are responsible for more than 90% of all cases of non-bacterial epidemic gastroenteritis(Kapikian et al., 1972; Kapikian, A. Z. et al., Chapter 25 in *Fields Virology*, Fields, B. N. et al., Eds., 1996; Pang, X. L. et al., *Pediatr. Infect. Dis. J* 18:420-426, 1999; Pang, X. L. et al., *J. Infect Dis.* 181(Supp. 2):S288-S294, 2000; Fankhauser, R. L. et al., *J. Infect. Dis.* 178:1571-1578, 1998; Glass, R. I. et al., *J. Infect. Dis.* 181(Supp. 2):S254-S261, 2000; Hedlund, K. O. et al., *J. Infect. Dis.* 181(Supp. 2):S275-S280, 2000; Koopmans, M. et al., *J. Infect. Dis.* 181(Supp. 2):S262-S269, 2000; Inouye, S. et al., *J. Infect. Dis.* 181(Supp. 2):S270-S274, 2000). There are no current therapeutic drugs or vaccines for these important human pathogens. *Sapoviruses* are typically associated with sporadic cases of pediatric gastroenteritis (Pang et al., 1999; Pang et al., 2000). Two other calicivirus genera, *Vesiviruses* and *Lagoviruses*, contain animal viruses exclusively. Calicivirus genomes typically contain a large 5' open reading frame (ORF1) encoding a nonstructural polyprotein, followed by ORF2 encoding a single capsid protein. ORF2 is either in frame with ORF1 or present as an independent ORF. While the 5' end of ORF1 shows extensive sequence diversity, the remainder of ORF1 contains motifs arranged in a specific order conserved between caliciviruses and picornaviruses. ORF3, encoding a basic protein, is present at the 3' end of the genome preceding a poly-A tract (Clarke, I. N. et al., *J. Infect. Dis.* 181(Supp. 2):S309-S316, 2000).

The unknown pathogen was passaged into RAG/STAT-/- and IFNαβγR-/- mice and caused lethal disease within 30 days of inoculation (A), characterized histologically by meningitis (C), vasculitis of the cerebral vessel (D), and encephalitis (E) compared to mock-infected brain (B). (B, C) RAG/STAT-/- mice; (D, E) IFNαβγR-/- mice. Brain homogenate from an infected RAG/STAT-/- mouse was passed into 129 wild-type mice (A) and sera of these mice harvested 35 days later tested negative for mycoplasma, Sendai virus, reovirus type 3, Theiler's mouse encephalomyelitis virus (GDVII strain), lymphocytic choriomeningitis virus, pneumonia virus of mice, minute virus of mice, mouse hepatitis virus, ectromelia virus, epizootic diarrhea of infant mice, mouse cytomegalovirus, polyoma virus, K virus, orphan parvovirus, and mouse adenovirus.

Figure 2:
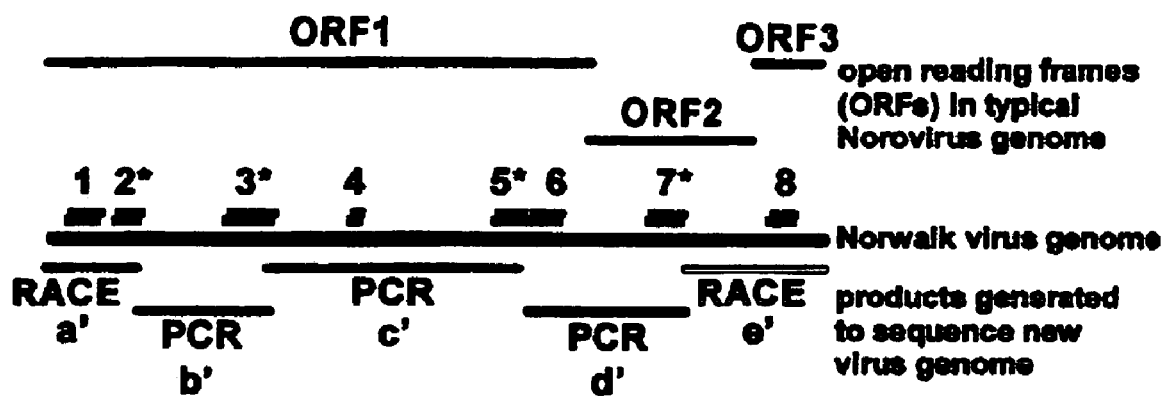
Figure 2:
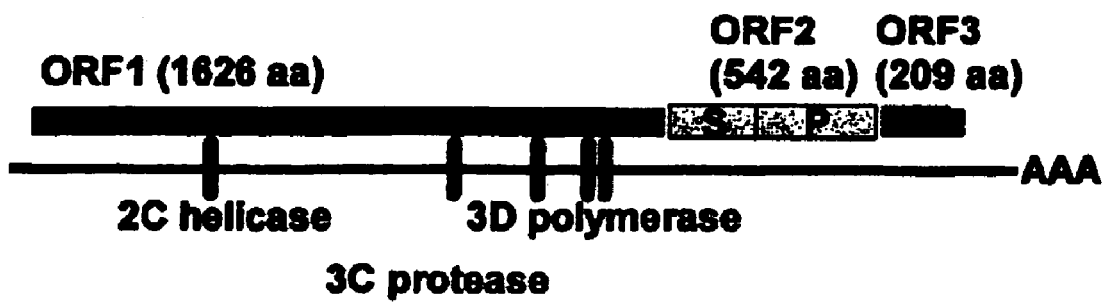
Figure 2:
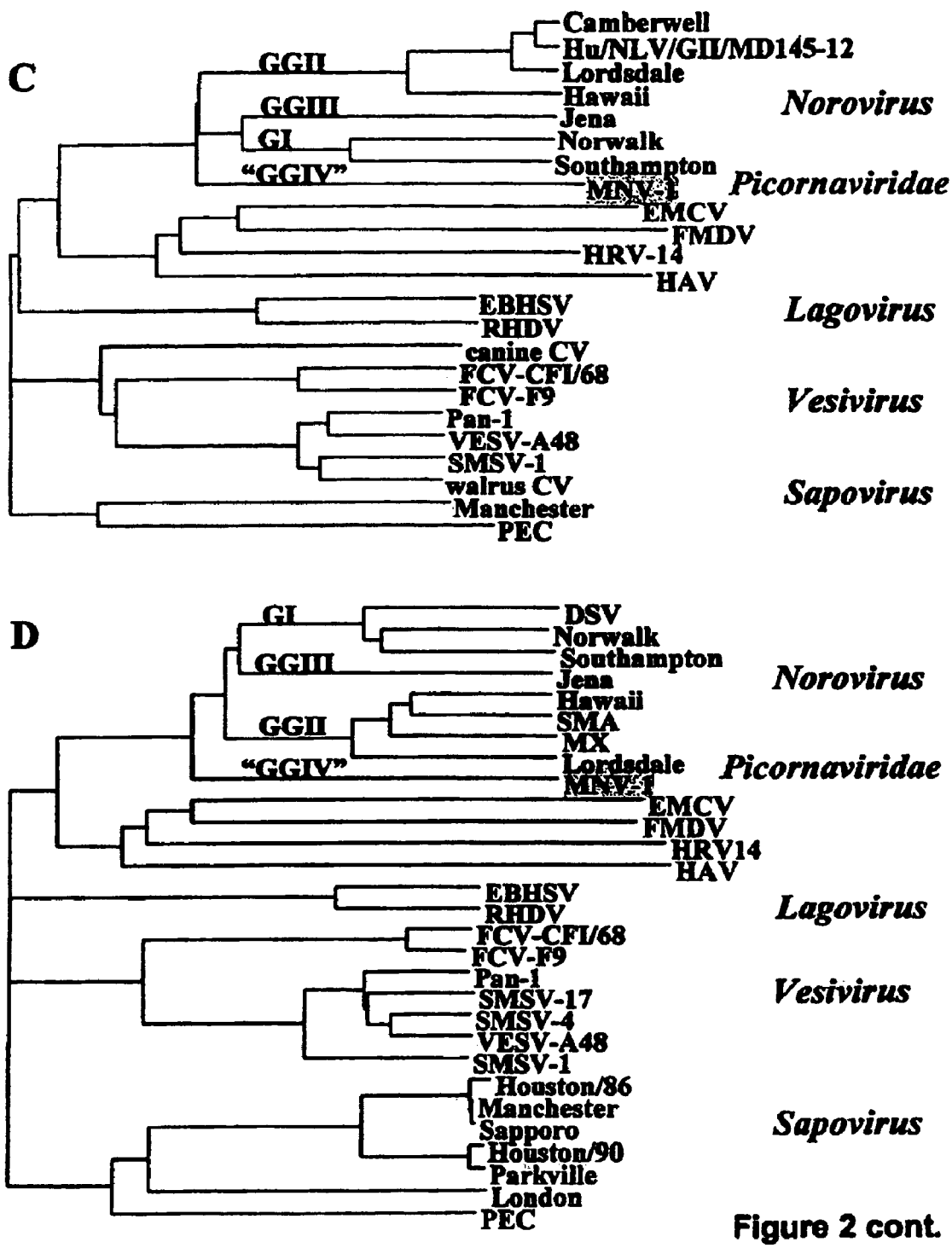

FIG. 2: Sequencing and phylogenetic analysis of the MNV-1 genome.

A) Double-stranded cDNA (dsDNA) from the brain of an infected IFNαβγR-/- mouse at passage 2 (FIG. 1) was prepared, digested with restriction enzymes, and ligated to adaptors containing PCR primer sequences to generate "tester" nucleic acids. dsDNA lacking linkers was prepared concurrently from a control brain to generate "driver" nucleic acids. Serial rounds of subtractive hybridization of tester in the presence of excess driver followed by PCR amplification of tester-specific sequences were performed to generate difference products (DP) one through four (DP1-DP4). DP3 and DP4 were cloned into pGEMT (Promega, Madison, Wis.), sequenced, analyzed using BLAST, and clones (1-8, FIG. 2A) homologous, but not identical, to calicivirus sequences were identified that spanned the Norwalk virus genome. Sequences within RDA clones (indicated by asterisks) were used to clone and sequence five fragments (a', b', c', d', e', FIG. 2A) of the MNV-1 genome after PCR or 5' and 3' RACE (Marathon cDNA amplification kit, Clontech, Palo Alto, Calif.). The 5' end of the genome was difficult to clone and consequently the first 15 nucleotides are based on a single sequence, while the remaining sequence has at least a 10-fold redundancy. This may explain why there is no start codon close to the 5' end as is expected based on comparison with other *Noroviruses*. B) Schematic of the final 7726 bp MNV-1 genome sequence with predicted open reading frames (ORFs). The locations of amino acid motifs in ORF1 are indicated: 2C helicase: GXXGXGKT (SEQ ID NO: 50); 3C protease: GDCG (SEQ ID NO: 51); 3D polymerase: KDEL (SEQ ID NO: 52), GLPS (SEQ ID NO: 53), YGDD (SEQ ID NO: 54). The putative S and P domains of the ORF2 encoded capsid protein were identified based on sequence alignments with Norwalk virus. AAA: 3' poly-A tail. C) Alignment of the complete MNV-1 genome with complete genomes of representative members of the four Caliciviridae genera and members of the most closely related virus family, the Picornaviridae. Specific members were chosen based on the 2000 taxonomy study by Green et al. (J Infect Dis '00 v. 81 p. S322). D) Alignment of the capsid protein sequence of MNV-1, done as in C. Note that the alignments in C and D were confirmed using other algorithms (data not presented).

Figure 3:
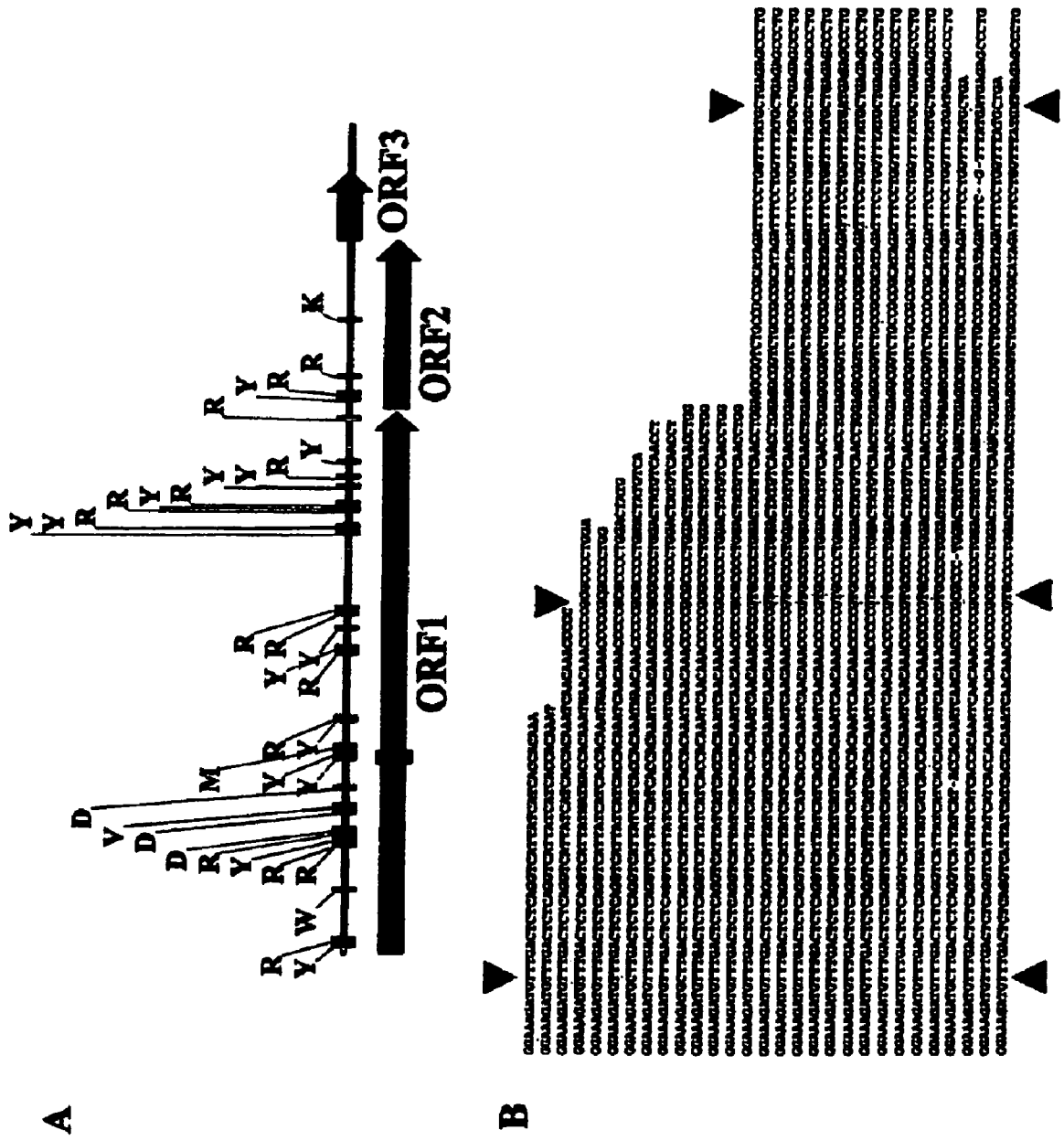

FIG. 3: Sequence variability of MNV-1.

A) All variable nucleotides within ORF1 and ORF2, based on sequence analysis of multiple clones of the entire MNV-1 genome, are depicted. These nucleotides had 20% or less variability between clones. B) Sequences of individual clones spanning nucleotides 1767 to 1893 (solid box on ORF1 in panel A), with variable positions highlighted with arrowheads SEQ ID Nos:21-48). The consensus sequence of MNV-1 is shown at the bottom (bold type) (SEQ ID NO:49), with variable nucleotides highlighted by arrowheads.

Figure 4:
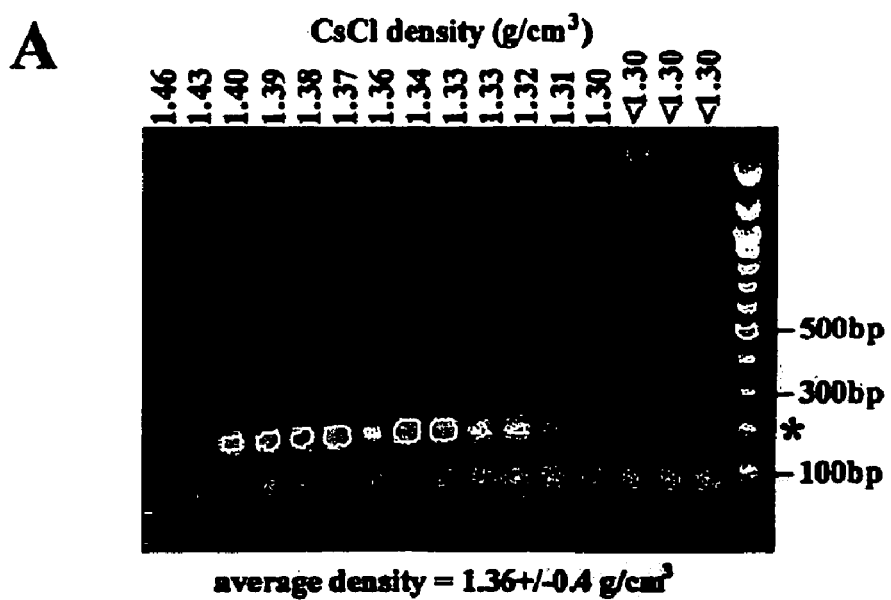
Figure 4:
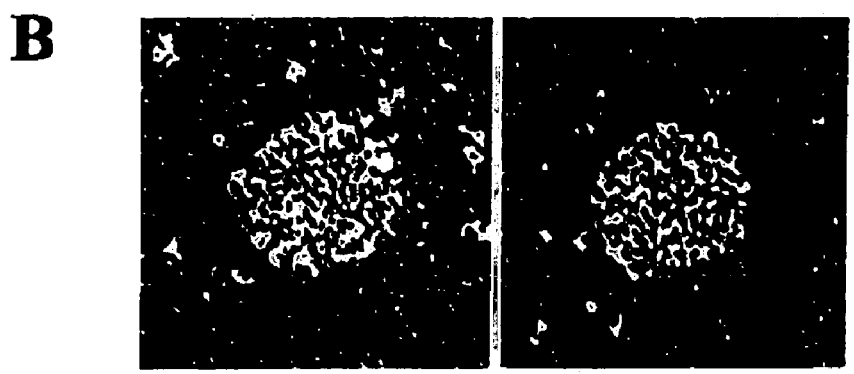
Figure 4:
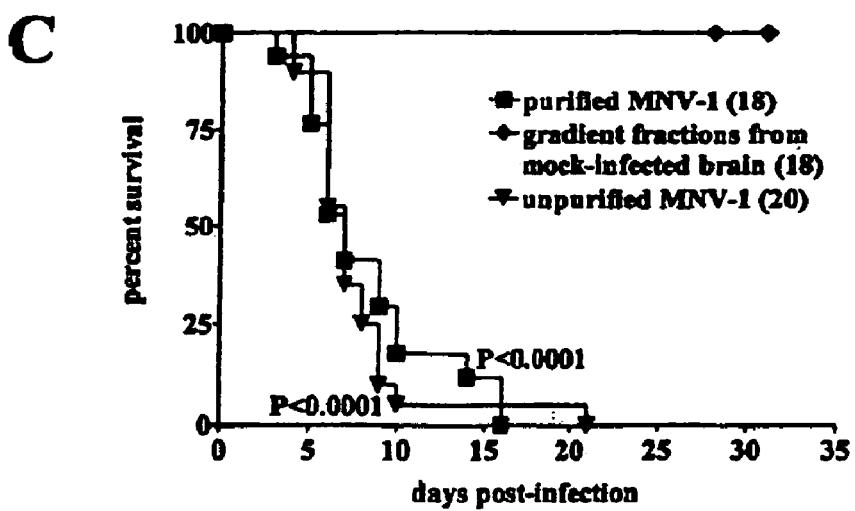

FIG. 4: Purification and pathogenicity of MNV-1.

MNV-1 was purified from an infected IFNαβγR-/- mouse brain homogenate by CsCl density gradient centrifugation. As a control, mock-infected mouse brain homogenates were processed similarly. (A) Determination of the average buoyant density of genome-containing MNV-1 particles. Dialyzed gradient fractions were analyzed by MNV-1 specific RT-PCR (Titanium one-step RT-PCR kit, Clontech, Palo Alto, Calif.) and products were separated on a 1% agarose gel. Primers were chosen in ORF1 to yield an expected product of 184 bp (indicated by the asterisk). (B) MNV-1 virions visualized by EM. Samples were absorbed onto formvar/carbon-coated grids for 1 min. The grids were washed in dH$_2$O, stained with 2% aqueous uranyl acetate (Ted Pella Inc., Redding, Calif.) for 1 min, and air dried prior to viewing on a JEOL 1200EX transmission electron microscope (JEOL USA, Peabody, Mass.). (C) Survival of RAG/STAT−/− mice infected i.c. with unpurified, or purified MNV-1, as well as gradient fractions from mock-infected brain. The P values for mock versus infected mice are indicated. Statistical analyses were performed using GraphPad Prism software.

Figure 5:
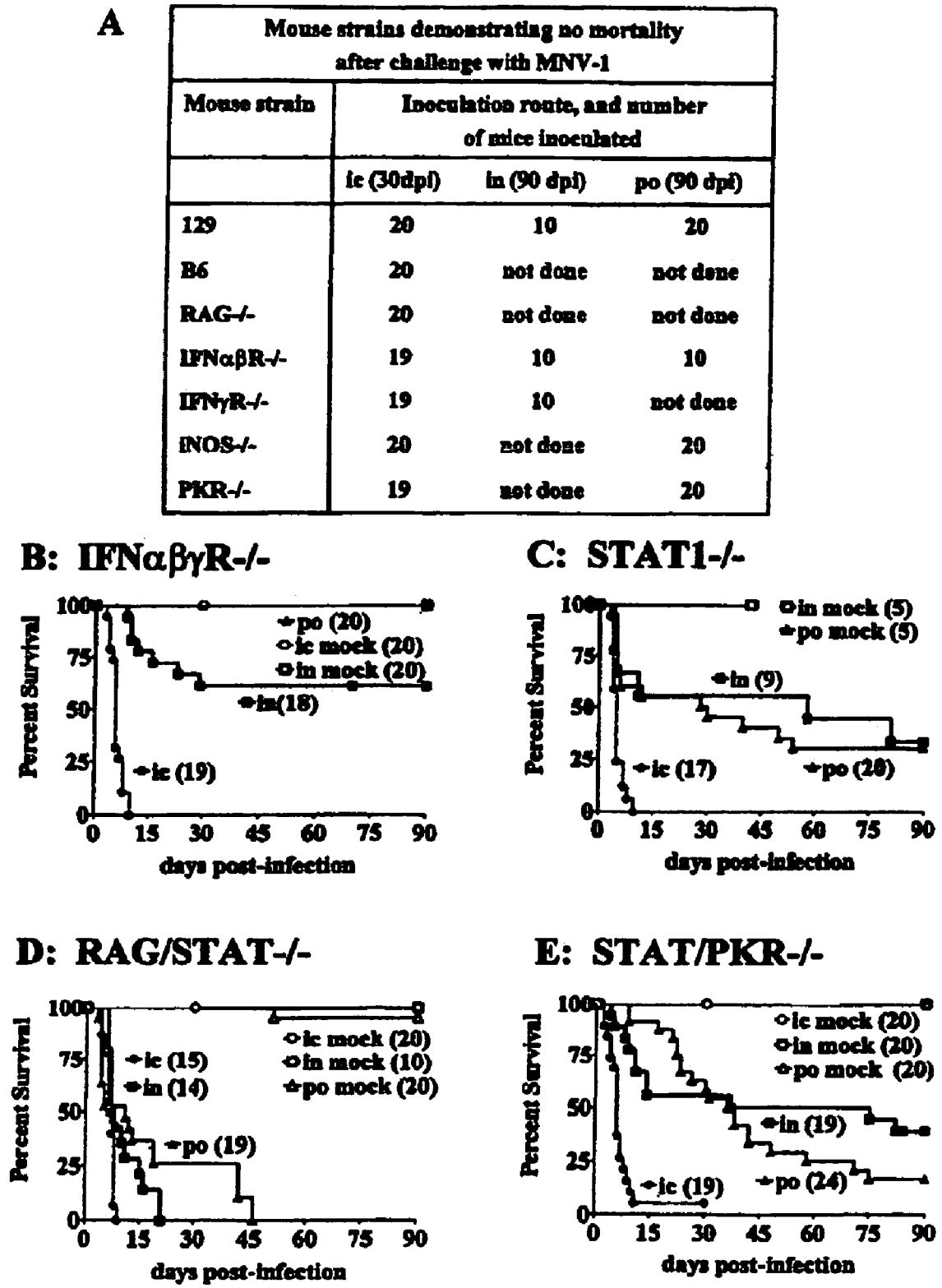

FIG. 5: IFNαβ or IFNγ receptors and STAT1 are required to protect from lethal MNV-1 challenge.

A MNV-1 stock was prepared as a brain homogenate from 17 IFNαβγR−/− mice inoculated i.c. three days previously with brain homogenate from a passage 2 (FIG. 1) mouse. Infected brains were homogenized in sterile PBS and filtered through a 0.2 µm filter. Brains from five IFNαβγR−−/− mice inoculated i.c. with uninfected brain tissue were used to generate a mock virus stock. Mice of various strains were inoculated with MNV-1 or mock-inoculated using 10 µl intracerebrally (ic), 25 µl intranasally (in), or 25 µl perorally (po). A number of mouse strains did not show increased mortality compared to wild-type 129 controls (A). The survival after inoculation with MNV-1 or mock virus is shown for IFNαβγR−/− mice (B), STAT1−/− mice (C), RAG/STAT−/− mice (D), and STAT1/PKR−/− mice (E). All p values for mock versus infected groups were ≦0.0001 except: IFNαβγR−/− i.n.: p=0.002; STAT1−/− i.n.: p=0.097; and STAT1−/− p.o.: p=0.034. Statistical analyses were performed with GraphPad Prism software.

FIG. 6: Generation of MNV-1 virus-like particles.

A) Western blot analysis of cell lysates from High-Five cells infected with recombinant baculovirus expressing the MNV-1 capsid protein (see Example 9) or a control baculovirus expressing the LacZ cassette (negative control). Proteins were detected by ECL Plus after incubation with serum from a MNV-1 infected mouse followed by a HRP-labeled secondary antibody. The size of the molecular weight marker is indicated on the right. B)-D) Electron microscopy of negatively stained VLPs. Supernatants of High-Five cells infected with a control baculovirus expressing LacZ (B), recombinant baculovirus expressing the MNV-1 capsid protein (C), or VLPs purified from these supernatants (D) were stained with uranyl acetate and photographed at a magnification of 50,000×.

Figure 7:
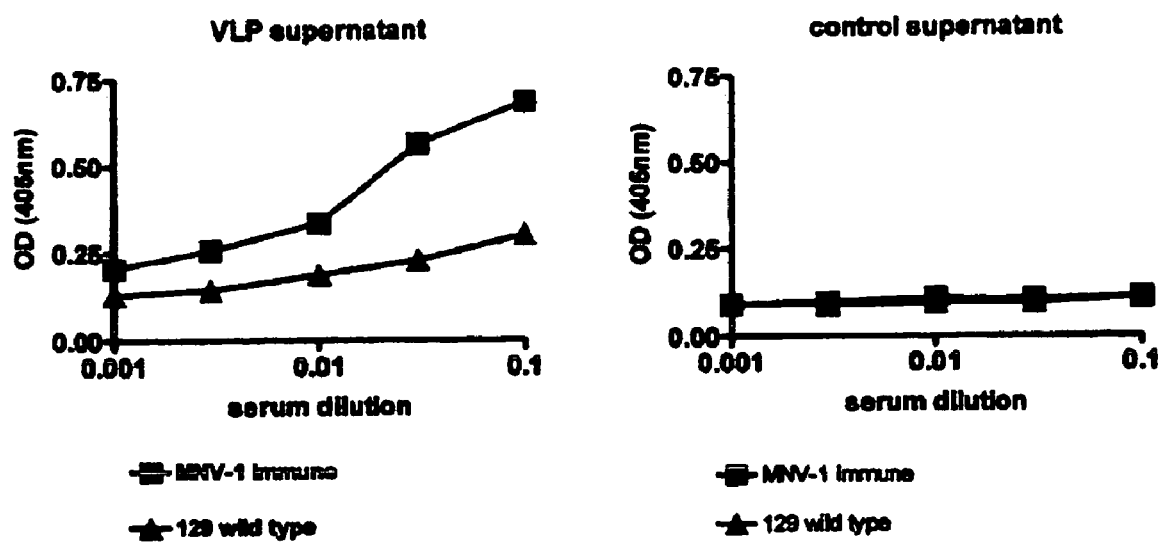
Figure 7:
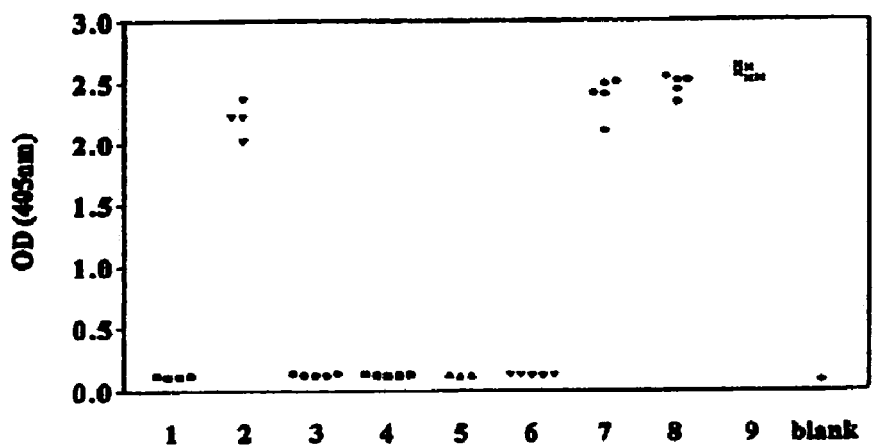

FIG. 7: Reactivity of mouse serum against MNV-1 VLP supernatants or cell lysates by ELISA.

Supernatants of High-Five cells infected with recombinant baculovirus expressing the MNV-1 capsid protein or LacZ expressing control were coated on ELISA plates. A) Analysis of half-log serial dilutions of serum from MNV-1 infected mice or 129 wild type mice. B) Analysis of 1:10 dilution of several cages of STAT−/− mice. Each dot represents one mouse. Reactivity was assessed after incubation with a HRP-coupled secondary antibody and calorimetric detection at 405 nm. Cages 1, 3, 4, 5 and 6 contained seronegative mice. Cages 2, 7, 8, and 9 contained seropositive mice.

FIG. 8: Tissue MNV-1 RNA levels after infection via different routes.

Four IFNαβγR−/− mice were inoculated with MNV-1 i.c. (10 µl), p.o. (25 µl), or i.n. (25 µl). Two mice were sacrificed at both 2 and 7 dpi and lung (Lu), intestine (Int), brain (Br) and feces were collected. RNA was extracted from each organ, and cDNA was synthesized and used (5 ng) in triplicate real time PCR reactions. Primers specific to a 131 nucleotide region of ORF1 were used (sense=cagtgccagccctcttat (SEQ ID NO:19); antisense=gtcccttgatgaggagga (SEQ ID NO:20)). Signal was compared to a standard curve generated using a plasmid containing target sequences. Triplicate reactions were performed using GAPDH primers to verify equivalent amounts of starting template (not shown). The levels of virus RNA as $\log_{10}$ MNV-1 genome copies are shown (open bars=2 dpi, solid bars=7 dpi, *-undetectable levels).

FIG. 9: Immunohistochemical staining of spleen sections from MNV-1 infected mouse. Formalin-fixed spleen sections from a STAT1−/− animal 3 days after p.o. inoculation with MNV-1 were stained with either immune polyclonal rabbit serum inoculated with bacterially expressed MNV-1 capsid protein (left panel), or with the preimmune serum from the same rabbit (right panel). Immunohistochemistry was performed with the PerkinElmer™ TSA™-Plus DNP (HRP) System, according to the supplied protocol. Primary antibodies were used at a 1:25 dilution. Positive cells are indicated by arrows.

Figure 10:
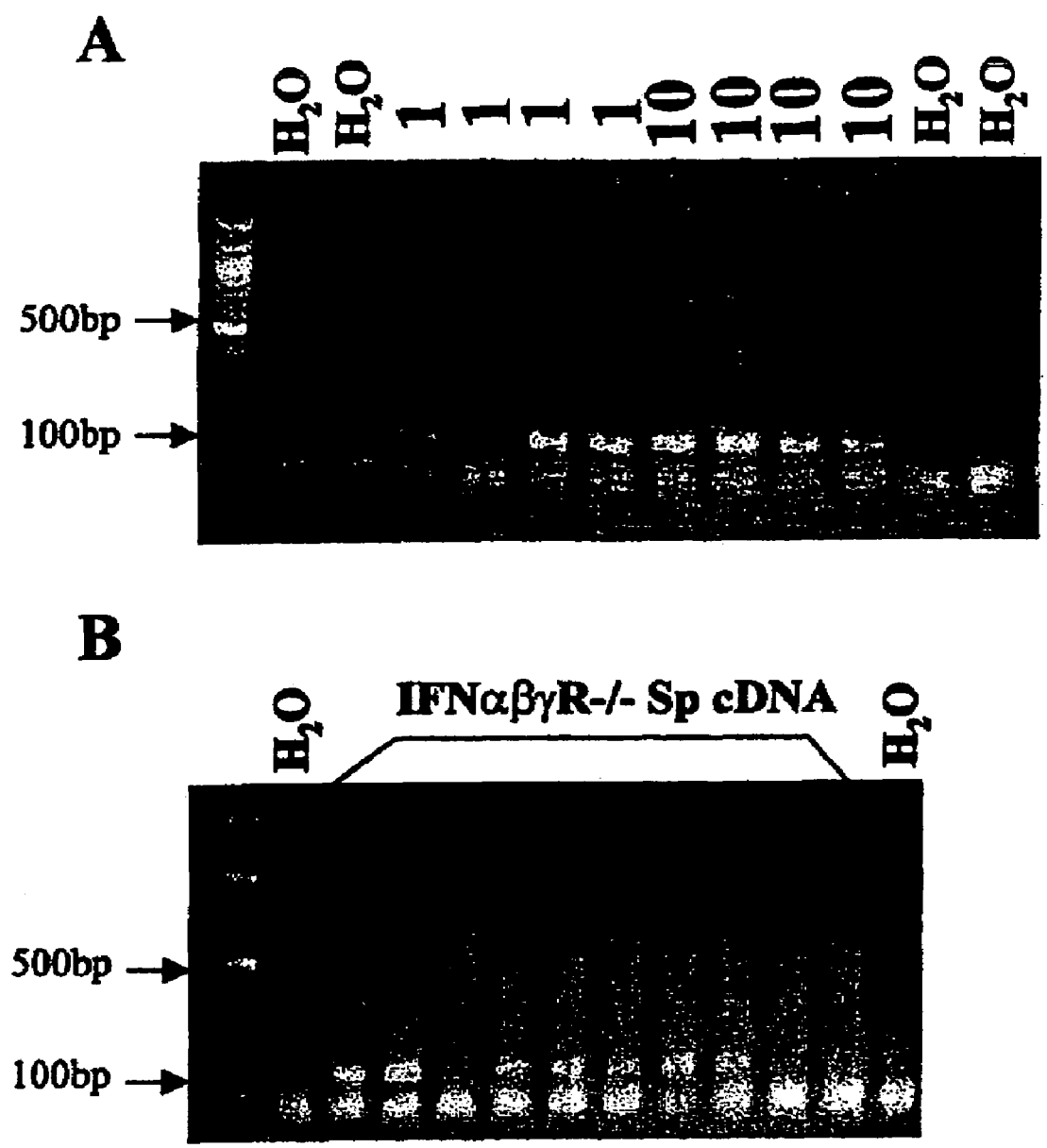

FIG. 10: Single copy sensitivity of MNV-1 cDNA detection by nested PCR assay. Nested PCR primers specific to a region of MNV-1 ORF2 were designed (outer-sense=gcgcagcgccaaaagccaat (SEQ ID NO:15); outer-antisense=gagtcctrtggcatgctacccagg (SEQ ID NO:16); inner-sense=gccgccgggcaaattaacca (SEQ ID NO:17); and inner-antisense=ggcttaaccccctaccttgccca (SEQ ID NO:18)). A) Multiple PCR reactions with either 1 or 10 copies of a plasmid containing the appropriate region of MNV-1 were performed. 3/4 and 4/4 reactions were positive for 1 and 10 copies, respectively. The expected size of the PCR product is 153 bp. B) cDNA was generated from spleen tissue of 10 IFNαβγR−/− mice and 1 µg of each was used in nested PCR reactions (7/10 samples were positive). All water controls are negative.

DESCRIPTION

Figure 1:
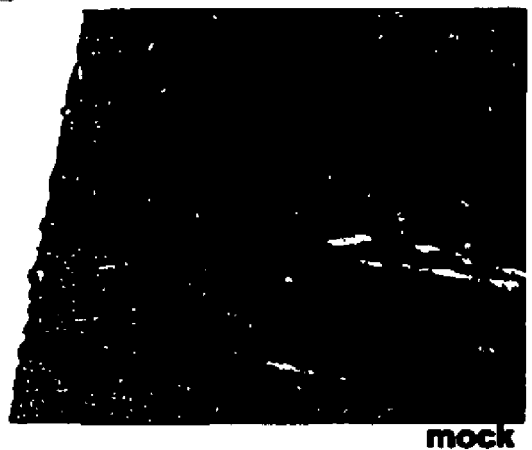
FIG. 1: Passage of a new pathogen by intracranial inoculation in RAG/STAT-/- and IFNαβγR-/- mice.
Figure 1:
Figure 1:
Figure 1:

It has been discovered that mice doubly deficient in STAT1 and RAG2 (RAG/STAT) contained an infectious pathogen that caused severe encephalitis and could be serially passaged by intracerebral (i.c.) inoculation (FIG. 1). Lethal infection was associated with encephalitis, vasculitis of the cerebral vessels, meningitis, hepatitis, and pneumonia (FIG. 1 and data not shown). Disease was passed by filtered samples, suggesting the presence of a virus (FIG. 1A). Sera of 129 mice infected with the putative virus tested negative for an extensive panel of mouse pathogens (see legend of FIG. 1). Brain homogenate from an infected RAG/STAT−/− mouse was passed into 129 wild-type or IFNαβγR−/− mice before and after filtration. A full work-up was performed on mice from passages 1 and 2, including histopathology, electron microscopy, standard clinical virology and microbiology work-ups, as well as special stains of histology sections (GMS, AFB [acid-fast bacilli], Gram stain). All of these failed to reveal the nature of the pathogen.

The pathogen is more virulent in mice lacking both the interferon αβ (IFNαβ) and the interferon γ (IFNγ) receptors (IFNαβγR−/−, [2]) than in wild-type mice (see below) and it passes through a 0.2 µn filter (see above and FIG. 1A). The pathogen does not appear to cause cytopathic effect on HeLa cells, Vero cells or murine embryonic fibroblasts (including those lacking IFN receptors or STAT1). These data suggest that a previously unknown IFN-sensitive but non-cultivatable pathogen that was <0.21 μm in size was present in diseased mice.

Identification and Sequencing

To identify the new pathogen a previously published representational difference analysis protocol (RDA) was used (See Pastorian et al., *Anal. Bicochem.* 283:89-98 (2000), which is hereby incorporated in its entirety). Double-stranded cDNA (dsDNA) from the brain of an infected IFNαβγR−/− mouse at passage 2 (FIG. 1) was prepared, digested with restriction enzymes, and ligated to adaptors containing PCR primer sequences (tester) (see Pastorian protocol for sequences of RDA primers). Control dsDNA lacking linkers was prepared concurrently from a control brain (driver). Serial rounds of subtractive hybridization of tester in the presence of excess driver followed by PCR amplification of tester-specific sequences were performed to generate difference products (DP) one through four (DP1-DP4). DP3 and DP4 were cloned and sequenced. Three of 24 clones from DP3 and ten of 48 clones derived from DP4 had significant homology to multiple caliciviruses (data not shown). These RDA clones spanned the Norwalk virus genome (FIG. 2A), but were not identical to any known full or partial calicivirus sequence, demonstrating that we had identified a novel calicivirus. This new virus is referred to herein as murine *Norovirus*-1 (MNV-1).

To determine the relationship of MNV-1 to other caliciviruses, the MNV-1 genome was cloned and sequenced from cDNA of an infected mouse brain using a combination of 5' and 3' RACE and PCR (FIG. 2A). Sequencing was performed in both directions with 10-fold redundancy to obtain a consensus sequence with the exception that the 5' 15 nucleotides were obtained from a single clone. The assembled genome included 7726 bp of unique sequence plus a 3' polyA tail, and contained the expected three ORFs conserved across the Caliciviridae (FIG. 2B). Phylogenetic analysis using the CLUSTAL W algorithm, and other algorithms including PAUP, aligning either the complete genome sequence (FIG. 2C) or the capsid protein sequence (FIG. 2D) of MNV-1 with corresponding sequences from members of the four calicivirus genera and several members of the Picornaviridae family revealed that MNV-1 is a *Norovirus* that does not cluster within previously identified genogroups (FIG. 2C, D)(Green K Y JID 181 S322-330). Therefore, it is proposed that MNV-1 is exemplary of a new *Norovirus* genogroup.

Thus, disclosed herein is a pathogen that infects mice, referred to herein as Murine *Norovirus*-1 (MNV-1). MNV-1 is both a unique *norovirus,* and is the first member of a new genogroup of *Noroviruses.* An exemplary sequence for the MNV-1 virus and genogroup is provided as SEQ ID NO:1, which is a consensus sequence representative of the full length MNV-1 genome as determined from a series of clones derived by PCR or RACE analysis from RNA derived from the brain of an infected mouse. Thus, one embodiment comprises an isolated RNA sequence as shown in SEQ ID NO:1. An additional embodiment comprises sequences of MNV-1 isolates that vary from the sequence in SEQ ID NO:1 by an amount determined by both sequence analysis and current understanding of the relatedness of different caliciviruses (see below). One embodiment comprises the viruses related directly to MNV-1 as viral quasispecies. Another embodiment comprises other members of the MNV-1 genogroup of which MNV-1 is the defining member. The criteria for viral quasispecies and viral genogroup are defined below, and serve to specifically set criteria for the MNV-1 embodiments described herein.

RNA viruses vary during infection due to errors made by the viral RNA-dependent RNA polymerase. Thus, MNV-1 (a positive-strand RNA virus) may be expected to vary during replication into a quasispecies comprising multiple viruses with sequences closely related to, but not identical to, the sequence of the original infecting virus. Thus, some embodiments of MNV-1 include viruses with sequences that vary from the sequence provided in SEQ ID NO:1 by an amount consistent with variation within a calicivirus quasispecies. The level of variation from the MNV-1 consensus SEQ ID NO:1 that still is considered by those skilled in the art to be the same virus (since these viruses always exist as quasispecies) is 5-7% (Radford et Al. Veterinary record Jan. 29, 2000 pp 117 on, Radford et al Vet Record Oct. 20, 2001 pp 477 on). Thus, an embodiment comprises the MNV-1 viral quasispecies of sequences that vary from our initial consensus sequence (SEQ ID NO:1) by no more than 5%. It has been confirmed that there is significant variance in MNV-1 nucleotide sequence even within a single infected animal (FIG. 3). To show this, a portion of the primary data from which the 10-fold redundant consensus sequence SEQ ID NO:1 was derived is presented. It was found that over the highly conserved ORF2 region, there are multiple sites at which there is sequence variation (FIG. 3A). A portion of the sequence data is presented in FIG. 3B for a region within which sequence variation was found. The frequency of variation at the sites shown in boxes is greater than that observed at multiple other sites (e.g. the remainder of the sequence in FIG. 3B), showing that these variations represent true biological variation rather than PCR artifacts or sequencing errors. Thus, MNV-1 does exist as a quasispecies.

Further embodiments comprise viruses with an amount of variance from SEQ ID NO:1 that is consistent with variation within a genogroup, and less than the variation observed between genogroups. For caliciviruses, genogroup and genus definition has been developed and officially set by the International Committee on the Taxonomy of viruses (ICTV) and research in the field has led to definitions of the amount of variation in sequence that is expected within a single genogroup as opposed to between viruses of different genogroups (K. Y. Green et al JID 2000 S322-330). Because nucleotide sequences can vary without causing variation in amino acid sequence, relatedness at the nucleotide level is a preferred method for distinguishing between genogroups or within a quasispecies (see above). Nucleotide identity within a genogroup of *Noroviruses* has been established as greater than 80% within the highly conserved capsid protein (ORF2) gene (J. Vinje et al Arch Virol (2000) 145:223-241). Thus, viruses that differ by more than 20% at the nucleotide level from a member of a genogroup (in this case from the MNV-1 sequence in SEQ ID NO:1) are not members of the genogroup. Nucleotide identity between genogroups is 64%-78% or less. Therefore, the genogroup to which MNV-1 belongs comprises viruses that vary by no more than 20% from the MNV-1 sequence within the capsid region. Similar reasoning applies to other conserved regions of the genome including the RNA dependent RNA polymerase gene. Therefore, our use of the capsid sequence for the definition of genogroup is standard.

Further embodiments include RNA sequences that are at least about 80% identical to SEQ ID NO:1, where the % identity is determined using Vector NTI AlignX program. Other embodiments include an isolated DNA sequence, or fragments thereof, identical to or complementary to SEQ ID NO:1, and isolated DNA sequences at least about 80% identical to or complementary to SEQ ID NO:1. Further embodiments comprise sequences between 80% and 100% identical to SEQ ID NO:1, and sequences complementary thereto.

Additional embodiments comprise fragments of any of the above mentioned sequences, such as may be used, for example, as primers or probes. Examples of such sequences include the primers listed in legends to FIGS. 8 and 10 that were used to detect virus infection in animals by nested PCR (FIG. 10) or to determine the amount of MNV-1 genome in a tissue by the use of real time PCR (FIG. 8). These primers will be useful for detection of MNV-1 infection in commercially bred mice and for quantitation of MNV-1 in tissues after trials of antiviral agents or vaccines. Such primers and probes are selected such that they are substantially complementary to a target sequence, wherein the target sequence consists of coding sequence of MNV-1. Here, substantially complementary means that the primer or probe is sufficiently complementary to the target sequence that it will hybridize to the target sequence under highly stringent conditions. As used herein, highly stringent conditions are as defined in the nested and real time PCR protocols exemplified in FIGS. 8 and 10. For hybridization in blots as opposed to PCR reactions, stringent refers to: hybridization at 68 degrees C. in 5×SSC/5× Denhardt's solution/1.0% SDS, and washing in 0.2×SSC/1.0% SDS at room temperature. Such probes and primers are useful, for example in various assays for detecting the presence of MNV-1 (FIG. 10) and determining how much MNV-1 is in a particular sample (FIG. 8). Other assays for which such primers or portions of MNV-1 sequence would be useful include Northern and Southern hybridization blot assays, additional PCR assays (e.g. degenerate PCR using primers with degenerate nucleotides at specific sites within the PCR primer to detect viruses within the MNV-1 genogroup but not identical to the MNV-1 sequence in SEQ ID NO:1), transcription-mediated amplification assays and the like, and as positive controls and internal standards for commercial assays to detect the presence of MNV-1 in mice or after treatment with anti-viral agents or vaccines.

A feature that distinguishes the human *Noroviruses* from the *Sapoviruses* are the cup-shaped depressions on the virion surface that gave the calicivirus family its name (calyx=cup in Latin). *Sapovirus* capsids show these characteristic cup-shaped depressions by electron microscopy (EM), while *Norovirus* capsids have a feathery appearance. To visualize MNV-1 virions, MNV-1 was purified from the brain of an infected IFNαβγR−/− mouse on CsCl gradients (FIG. 4). Gradient fractions containing MNV-1 genome were identified by RT-PCR (FIG. 4A), revealing a buoyant density of MNV-1 of 1.36 g/cm$^3$ ×/− 0.04 g/cm$^3$ (n=3 experiments), in close agreement with the published buoyant densities of *Noroviruses* (1.33-1.41 g/cm$^3$). Analysis of these gradient fractions by EM revealed particles with a diameter of 28-35 nm (FIG. 4B), similar to the known size (26-32 nm) of *Norovirus* particles in negatively stained preparations. The particles were icosahedral and had the same feathery surface morphology as *Noroviruses* but lacked the cup-like depressions characteristic of *Sapoviruses*. Gradient fractions prepared from mock-infected brain did not contain these particles (data not shown).

To test the pathogenicity of MNV-1, mice were infected i.c. with CsCl gradient purified MNV-1. These virions were infectious since 18/18 RAG/STAT mice inoculated with them died, while 18 of 18 mice inoculated with gradient fractions prepared from a mock-infected brain survived (FIG. 4C). Mice inoculated with gradient-purified virions showed encephalitis, meningitis, cerebral vasculitis, pneumonia, and hepatitis (data not shown). This mortality rate and pathology was similar to that observed previously in mice inoculated with unpurified brain homogenate (FIG. 4C and data not shown). The presence of disease in mice inoculated with CsCl-purified MNV-1 demonstrates that MNV-1 is the causative agent of the disease initially detected and passed (FIG. 1).

The MNV-1 genome comprises three open reading frames (ORFs). Analysis of the predicted coding sequence of ORF1 indicated a polyprotein with a molecular weight (MW) of 180.7 kDa and revealed the presence of multiple conserved motifs shared by caliciviruses and picornaviruses (FIG. 2B). ORF2 is separated from ORF1 by 32 nt and starts in the −1 frame relative to ORF1. It encodes a 542 aa protein with a calculated MW of 58.9 kDa and an isoelectric point of 5.19. When this gene was expressed in a recombinant baculovirus, virus-like particles (VLPs) were found in the supernatant of infected cells, demonstrating ORF2 encodes the capsid protein (FIG. 6). These VLPs provide a reagent for analysis of MNV-1 infection (see below). The predicted ORF3 encodes a basic protein (pI of 10.22) with a calculated MW of 22.1 kDa that overlaps by 2 nt with ORF2 and is expressed in the +1 frame relative to ORF1 but the −2 frame relative to ORF2.

Thus, further embodiments comprise the amino acid sequences encoded by ORF1, ORF2 and ORF3. These amino acid sequences are shown in SEQ ID NO:2, SEQ ID NO:3 and SEQ ID NO:4, respectfully. Additional embodiments comprise amino acid sequences that are encoded by viruses that vary from SEQ ID NO:1 by no more than 20% at the nucleotide level as defined above. The protein translation of such sequences will vary on a percentage basis depending on the placement of nucleotides within codons and the frequency of amino acids coded for by single versus multiple three base pair codons used by the translational machinery. Therefore the extent of variation of these embodiments is properly determined by defining the extent of total nucleotide variation accepted as defining the MNV-1 genogroup. Some embodiments comprise the nucleotide sequences that encode each of the amino acid sequences of SEQ ID NO:2, SEQ ID NO:3 and SEQ ID NO:4, including degenerate variants that encode those amino acid sequences. Additional embodiments comprise the nucleotide sequences of ORF1, ORF2 and ORF3 of MNV-1.

Additional embodiments include vectors capable of expression of any of the proteins encoded by MNV-1 or their variants as defined above. Examples of suitable vectors include baculovirus vectors, alphavirus vectors (e.g. Sindbis virus vectors, VEEV replicons), retroviral vectors, plasmids within which expression is driven from eukaryotic promoters, plasmids that generate short RNA sequences suitable for gene inactivation by RNAi technology, plasmids in which the presence of an RNA polymerase transcribes MNV-1 sequences (including the entire sequence) in order to provide RNA (including up to full length infectious RNA) for analysis or transfection into cells. Infectious RNA is defined as RNA, which, on transfection into eukaryotic cells, gives rise to intact infectious virus. Portions of the genome may also be expressed in this fashion for the generation of viral proteins or for analysis of the processing of MNV-1 viral proteins for the purpose of developing assays for identification of steps in viral replication that may serve as drug targets. Additional uses of expression vectors include generation of cells expressing viral proteins in a stable fashion for the purpose of screening anti-viral antibodies or for providing positive controls for assay for detection of anti-viral antibody in the serum.

As discussed above, expression of the capsid protein, i.e., the protein encoded by the sequence of ORF2, results in the formation of virus-like particles (VLPs). Thus, some embodiments comprise methods of producing VLPs. Such methods comprise transfecting a cell or animal with a vector that encodes the MNV-1 capsid protein, and recovering VLPs, or expression of the capsid protein from within the baculovirus genome such that the capsid protein is produced in insect cells infected with the baculovirus expressing the capsid protein. Further embodiments comprise MNV-1 VLPs. VLPs are useful, for example, for isolation of antibodies, analysis of the epitopes that antibodies recognize, and for cryo-EM and X-ray crystallography and other methods for determining the three dimensional structure of the MNV-1 capsid. VLPs may also be studied for potential use as a vaccine. In this setting they may be useful for mapping the specific conformational epitopes recognized by anti-viral antibodies and the specific peptides recognized by antiviral CD4 and CD8 T cells.

Antibodies

Some embodiments comprise antibodies that bind specifically to any of the various proteins encoded by the MNV-1 genome. Methods for producing antibodies are known in the art. Such antibodies may be either monoclonal or polyclonal. Antibodies can be used in various assays, such as for example ELISA assays, to detect the presence of MNV-1 in a sample. Samples include for example serum, saliva, feces, and tissues. In addition, antibodies may be utilized in methods for preventing lethal MNV-1 infection and studied for potential use as vaccines or anti-viral therapeutics.

An example of the use of antibodies and antibody detection assays is the demonstration that seroconversion can be detected by ELISA of serum using MNV-1 VLPs as the target antigen bound to the ELISA plate (FIG. 7). A further example is the demonstration that MNV-1 infection can be detected in specific cells by using immunohistochemistry to detect the binding of MNV-1 specific antibodies to infected cells (FIG. 9). This type of use may also be employed for detecting binding of virus to cells by FACS analysis. This in turn will provide an opportunity to identify the receptor for MNV-1. Identification of the MNV-1 receptor on the cell surface may provide important targets for anti-viral drug development. In addition, antibodies will be used for immunofluorescence and in-situ detection of virus infected cells.

Small Animal Model

The discovery of the first murine *Norovirus* provides the first small animal model for development and testing of pharmaceuticals and vaccines for treatment and prevention of a major human disease. This presents an opportunity to answer important questions regarding the pathogenesis of *Norovirus* infections, to determine the role and mechanisms of immunity in either protection against infection or immunopathology, to identify novel therapeutic targets for treatment of human calicivirus disease, and to better understand how innate immunity can control enteric virus infection. The mouse model can also be used in methods to identify agents that alter calicivirus infection and disease.

The course of human *Norovirus* infection strongly suggests that symptoms are caused by acute infection. Prominent amongst the clinical manifestations are vomiting and diarrhea with a mean incubation period of 24 hours and duration of 24-48 hours. Understanding of the viral and host mechanisms involved in the induction and clearance of human *Norovirus* disease is rudimentary. Acquired immunity can play a role in *Norovirus* resistance, but may not explain why certain individuals get severe disease while others do not. It may be that long-term immunity can be achieved, and the use of the MNV-1 virus in a small animal model provides the first opportunity to define such possible mechanisms. Infected individuals can develop short-term immunity to homologous virus, but the development of long-term immunity is questionable. An unexpected inverse relationship between pre-challenge antibody levels and susceptibility to infection has been reported in some studies (Parrino, T. S., et al., N. Engl. J. Med. 297:86-89, 1977; Johnson, P. C. et al., J. Infect. Dis. 161:18-21, 1990; Okhuysen, P. C. et al., J. Infect. Dis. 171: 566-569, 1995), while others have reported that circulating antibody does correlate with resistance to calicivirus infection (Lew, J. F. et al., J. Infect. Dis. 169:1364-1367, 1994; Ryder, R. W. et al., J. Infect. Dis. 151:99-105, 1985;Nakata, S. et al., J. Infect. Dis. 152:274-279, 1985). This controversy has led to studies showing that non-immune host factors, such as blood groups, influence susceptibility to infection(Hutson, A. M. et al., J Infect. Dis. 185:1335-1337, 2002). The discovery of MNV-1 provides a small animal model for the study of *Noroviruses*.

One embodiment is therefore the use of mice infected with MNV-1 as an approach to identifying the efficacy of vaccines or therapeutic agents. Mice would be infected with the newly discovered virus, and then treated with candidate agents and the outcome of the infection monitored using ELISA (FIG. 7), quantitative real time PCR for the viral RNA (FIG. 8), immunohistochemistry (FIG. 9), lethality (FIG. 5), or in situ hybridization to monitor the course of infection. Similarly, another embodiment is the use of mice infected with MNV-1 to test the efficacy of vaccination protocols against the virus. In this case, different vaccine preparations (including vectors expressing portions of the new virus genome or proteins from the virus or from human *noroviruses* that cross react with proteins from the mouse virus) would be administered to infected mice and the effect of vaccination on the course of the infection monitored using ELISA (FIG. 7), quantitative real time PCR for the viral RNA (FIG. 8), immunohistochemistry (FIG. 9), lethality (FIG. 5), or in situ hybridization. As it is not practical to perform such experiments in humans, the capacity to perform these types of screens for in vivo efficacy of therapeutics or vaccines is not possible without the use of this newly described virus.

One embodiment includes nested PCR assays for determining presence, absence or quantity of MNV-1 in a tissue, organ or feces sample of a mouse, wherein the organ is selected from the group consisting of lung, intestine and brain. These methods comprise subjecting a cDNA synthesized from RNA comprised by the tissue, organ or feces of the mouse to a first amplification reaction using a first sense primer and a first anti-sense primer, wherein the first sense primer and the first anti-sense primer hybridize to target sequences comprised by MNV-1. The reaction product of the first amplification reaction can then be subjected to a second amplification reaction using a second sense primer and a second anti-sense primer, wherein the second sense primer and a second anti-sense primer hybridize to target sequences comprised by a reaction product of the first amplification reaction, if MNV-1 is present in the sample.

In addition, the discovery of MNV-1 and the generation of a consensus sequence will enable construction of an infectious clone for MNV-1. One embodiment is therefore generation of such an infectious clone from the current cloned and sequenced genome or from sequences that vary within the limits described above for the MNV-1 quasispecies or MNV-1 genogroup. Such a clone can be used to develop various screening assays for MNV-1 antiviral agents and targets for antiviral drug development and vaccines for prevention of infection or antibodies for therapy of disease, and also may be used to study certain aspects of the viruses infection cycle including binding, entry, uncoating, negative strand RNA synthesis, positive strand RNA synthesis, subgenomic RNA synthesis, synthesis of structural and non-structural proteins, viral assembly and viral egress to be studied and used to develop screens for antiviral drugs that might have uses in preventing or treating *Norovirus* induced disease. In addition, placement of portions of human *Noroviruses* into an infectious clone for MCV-1 (e.g. substituting proteins such as the capsid of RNA polymerase of the human virus into the mouse virus infectious clone) will allow the murine virus to be humanized and potentially still used in mice. This will allow screening of therapeutic agents that target the functions of human *norovirus* proteins in an animal model. This is possible only through the combined use of an infectious MNV-1 clone as a vector for expressing functional proteins and a small animal model which allows assessment of the effects of therapeutic agents or vaccines on the course of infection with such "humanized" forms of the mouse calicivirus MNV-1.

In addition, the use of the newly discovered MCV-1 virus in mice with different immune deficiencies will allow identification of host proteins that play a role in control of *Norovirus* infection. An example of this is the detection of the critical role of STAT-1 in resistance to MNV-1 infection (Working Example 14, FIG. 5). Identification of such host proteins could allow development of targeted therapeutic agents that enhance specific parts of the host immune response as a way to treat or prevent *Norovirus* disease. Such embodiments include, for example, use of the virus in mice with deficiencies in specific parts of the immune system in order to identify mice that have increased susceptibility or increased resistance to infection by MCV-1. Such embodiments would be useful for identifying immune protective or immunopathologic aspects of the host response and thereby inform searches for vaccines or therapeutic agents that could prevent or treat *Norovirus* infection. An example would be targeting enhanced STAT-1 function, based on the experiments in FIG. 5, for prevention of *Norovirus* disease in humans.

WORKING EXAMPLES

Example 1

Generation of MNV-1 Stock

After identification of MNV-1 in RAG/STAT and IFNαβγR-deficient mice, a brain homogenate from an IFNαβγR-deficient mouse at passage 3 was used for i.c. inoculations of 17 additional IFNαβγR-deficient mice. Brains of infected mice were harvested 3 days post-infection and homogenized in PBS. Homogenates were centrifuged at low speed and filtered through a 0.2 μm filter and the resulting supernatant was used in subsequent infections. For control experiments, brain homogenates of mock-infected mice were prepared similarly after injection of mice with uninfected mouse brain homogenate. (See FIG. 5).

Example 2

Purification of MNV-1 Virions

Homogenate from one MNV-1 infected brain was used for purification of MNV-1 virions while a mock-infected mouse brain was used as a control (FIG. 4). Homogenized brain was subjected to a cycle of freeze/thaw and two low speed centrifugations before filtration through 0.22 μm filter. Supernatants were centrifuged at 90,000×g for 2 hrs and the resulting pellets were incubated for 30 min at 37 C in 1 ml 1% Na-deoxycholate. The resulting material was mixed with CsCl to a final density of 1.36 g/cm$^3$ and centrifuged for 40 hrs at 150,000×g. Gradients were fractionated, their density determined with a refractometer, and dialyzed against a buffer containing 0.01M Tris-HCl, 0.15M NaCl, 1 mM CaCl$_2$, and 0.05M MgCl$_2$. (See FIG. 4).

Example 3

RNA Isolation, cDNA Synthesis, and RDA

Total RNA was isolated from a MNV-1 infected mouse brain using Trizol (Invitrogen, Carlsbad, Calif.) following the manufacturer's instructions. Double-stranded cDNA for use in RDA was synthesized from total RNA using the Superscript Choice System for cDNA synthesis (Invitrogen, Carlsbad, Calif.) and a combination of random hexamers and oligo dT primers. Single-stranded cDNA for quantitative PCR was generated using Supercript II (Invitrogen, Carlsbad, Calif.) following the manufacturer's recommendations. RDA was performed as described by Pastorian et al. (Anal. Biochem. 283:89-98, 2000) with the following modification. The QIAquick PCR purification kit (Quiagen, Valencia, Calif.) was used to remove unincorporated nucleotides and small cDNA species. Difference products from rounds 3 and 4 were cloned into the pGEM-T vector system (Promega, Madison, Wis.) following the manufacturer's instructions. Bacterial colonies were grown up and inserts were PCR amplified for sequencing. (See FIG. 2, 3 ).

Example 4

RT-PCR and Quantitative PCR

RT-PCR was performed with primers 445/1/AS6 (TC-CAGGATGACATAGTCCAGGGGCG)(SEQ ID NO:5) and 445/1/S6 (TGGGATGATTTCGGCATGGACAACG) (SEQ ID NO:6) using the Titanium one-step RT-PCR kit (Clontech, Palo Alto, Calif.) following manufacturer's recommendations. Quantitative PCR (FIG. 8) was performed with primers ORF1/RT1/S (cagtgccagccctcttat) and ORF1/RT1/AS2 (tc-ctcctcatcaagggac) that amplify a 132 bp segment of ORF1 outside of the predicted subgenomic RNA. This assay has a sensitivity of 100 viral genomes/μg cellular RNA or about 1 MNLV-1 genome per 1720 cell equivalents of RNA (estimating 1 μg cellular RNA/172,000 cells). The assay linearly quantitates genome over at least a 6-log range. (See FIG. 8).

Example 5

Cloning of the MNV-1 Genome

A combination of PCR and RACE was used to clone the MNV-1 genome (FIG. 2A). For internal sequence information, primers were constructed based on sequence information obtained through RDA and used to amplify and clone larger pieces of MNV-1 from 1$^{st}$ strand cDNA from a RAG/STAT mouse brain (passage 3). These PCR products were cloned into the pGEMT vector (Promega, Madison, Wis.) and universal M13 forward and reverse primers used for sequencing. Primer walking was applied when necessary. For the 5' and 3' ends of MNV-1, RACE was performed with the Marathon cDNA Amplification Kit (Clontech, Palo Alto, Calif.) using total RNA from the same RAG/STAT mouse brain (passage 3) as starting template. These products were cloned and sequenced as outlined above. A consensus sequence with at least 10-fold redundancy (except for the 5' end, see below) was constructed using the VectorNTI contig program. The 5' end of the genome was difficult to clone and consequently the first 15 nucleotides are based on a single sequence, possibly explaining why there is no start codon close to the 5' end as is expected based on comparison with other *Noroviruses*. (See FIG. 2).

Example 6

Cloning and Expression of the MNV-1 Capsid Protein in Bacteria

The MNV-1 capsid protein was PCR amplified from first strand cDNA from a RAG/STAT mouse brain (passage 3). The following primers C-pET1 (GTGGTGCTCGAGTGCG-GCCGCAAGCTTTATTATTGTTTGAGCATTCGGCCTG) (SEQ ID NO:7) and N-pET1 (ATCCGAATTCTAGATG-CACCACCACCACCACCACATGAGGATGAGTGATG-GCGCAG) (SEQ ID NO:8) containing HindIII and EcoRI restriction sites (underlined), respectively, and a 6 Histidine N-terminal tag (bold) were used in a 2 step PCR reaction (5 cycles 50 C, 30 cycles 60 C) in the presence of 5% DMSO. The resulting PCR product was ligated into a PCR blunt cloning vector (Zero Blunt PCR Cloning kit, Invitrogen, Carlsbad, Calif.) and transformed into DH5α CaCl$_2$ competent cells (Invitrogen, Carlsbad, Calif.). DNA was isolated from the resulting clones and diagnostic restriction digests followed by DNA sequencing confirmed the presence and sequence of the insert. The insert was cloned into the bacterial expression vector pET-30a (+) Novagen, Madison, Wis.) using the EcoRI and HindIII restriction sites. Next, BL21 (DE3) competent cells were transformed and protein was expressed following the manufacturer's protocol (Novagen, Madison, Wis.).

Example 7

Purification of Bacterially Expressed MNV-1 Capsid Protein

Following a 2 hour expression, protein was purified from inclusion bodies of bacterial cells using the BugBuster protein extraction reagent (Novagen, Madison, Wis.). His-tagged capsid protein was isolated from remaining protein by nickel column chromatography (Ni-NTA His Bind Resin, Novagen, Madison, Wis.) in the presence of 8M urea and protease inhibitors (protease inhibitor cocktail set III, Novagen, Madison, Wis.). Samples were dialyzed against 25 mM phosphate buffer (pH 6.0) and the purity of each preparation was assessed by SDS-PAGE and silver staining (Silver stain Plus kit, Biorad, Hercules, Calif.).

Example 8

Generation of Antisera in Rabbits

Rabbit sera was produced through Cocalico Biologicals, Inc. (Reamstown, Pa.). Basically, rabbits were injected with 100 μg bacterially expressed capsid protein in CFA (complete Freund's adjuvant) and boosted after a month once every month with 50 μg protein in IFA (incomplete Freund's adjuvant). Production bleeds were collected a week after each boost and before the start of injections. The same procedure is being used for generation of antibodies directed against virus-like MNV-1 particles.

Example 9

Cloning and Expression of the MNV-1 Capsid Protein in Baculovirus

The MNV-1 capsid protein was cloned into the baculovirus expression vector in an analogue way to the cloning into the bacterial expression vector. The following primers were used for initial 2 step PCR amplification (4 cycles at 50 C, 30 cycles at 64 C) of the MNV-1 capsid protein: N-Bac1 (CG GAATTCGGATGAGGATGAGTGATGGCGCA)(SEQ ID NO:9), C-Bac1 (TCTCGACAAGCTTTTATTGTMTGAG-CATTCGGCCT)(SEQ ID NO:10). The same restriction sites, EcoRI and HindIII (underlined) were used for cloning into the pFastBac1 vector (Invitrogen, Carlsbad, Calif.). Recombinant baculoviruses were made using the Bac-to-Bac Expression system (Invitrogen, Carlsbad, Calif.) following the manufacturer's instructions. Briefly, the recombinant vector plasmid containing the MNV-1 capsid protein was transformed into DH10Bac *E.coli* cells allowing for transposition of the gene of interest into the bacmid genome. Clones containing recombinant bacmids were identified by antibiotic selection and disruption of the lacZ gene. Recombinant bacmid DNA was then used for transfection of Sf9 insect cells. Recombinant baculoviruses were amplified for several rounds on Sf9 or Sf2 cells (Invitrogen, Carlsbad, Calif.) before infection of High-Five cells (Invitrogen, Carlsbad, Calif.) for protein expression. High-Five cells were infected for 5-7 days and supernatant were collected for purification of MNV-1 VLPs. Initial preparations were screened for the presence of VLPs by negative staining electron microscopy. VLPs were identified in the supernatants of several isolates (FIG. 6C). Two isolates with the highest amount of protein expression were chosen for further experiments. The amount of protein expression in each preparation was analyzed by SDS-PAGE and immunoblotting (FIG. 6A).

Example 10

Purification of MNV-1 VLPs

MNV-1 VLPs are purified from the supernatant of infected High-Five cells 7 days post-infection (FIG. 6D). The purification protocol is based on Leite et al. (Arch Virol, 1996, 141:865-875), which is hereby incorporated by reference. Briefly, protein in the cell supernatant is being precipitated using PEG 8000, and particles are purified using CsCl gradients. VLPs are dialyzed against 25 mM phosphate buffer, pH 6.0. Details of the protocol are being optimized at this point.

Example 11

Use of VLPs, Potential and Actual Targets of VLPs

VLP-containing insect cell supernatants are being used for ELISA to screen mouse sera (see ELISA below). VLPs will be used to generate rabbit antisera. Their role as potential vaccine will be investigated. They will also be used for three-dimensional structure determination of the MNV-1 capsid.

Example 12

ELISA Assay

This assay can be used to screen mice capable of eliciting an antibody response (FIG. 7). The assay was optimized for a maximal signal-to-background ratio. VLP-containing insect cell supernatants are used as antigens for coating ELISA plates over night at 4 C. Plates are blocked for two hours at 37 C with 3% BSA and washed with 0.1 5M NaCl+0.05% Tween 20. Sera from mice are diluted 1:100 and incubated for 1 hour at 37 C. After washing, wells are incubated for two hours at 37 C with a 1:1000 dilution of peroxidase-conjugated AffiniPure goat anti-mouse IgG (H+L) (Jackson ImmunoResearch Laboratories, Inc., West Grove, Pa.). Plates are developed after another round of washing by addition of the substrate 2,2'-Azinobis 3-ethylbenzthiazoline sulfonic acid (ABTS, Sigma-Aldrich Corp., St. Louis, Mo.) for 10 min, the reaction is stopped using 0.2N phosphoric acid, and quantified by reading the absorbance at 415 nm.

Example 13

Nested PCR Assay

This assay can be used to screen tissues of immunocompromised mice with no antibody response (FIG. 10). RNA is isolated from the tissue(s) of interest and $1^{st}$ strand cDNA is being made (see above). To sets of primers were designed with the following sequences: outer sense primer CCAAAAGCCAATGGCTCTGA (SEQ ID NO:11), outer antisense primer AGTTGAATGGGCTCCAGGGT (SEQ ID NO:12), inner sense primer CCGCCGGGCAAATTAACCAA (SEQ ID NO:13), inner antisense primer AGGTGGGCAAGGTAGGGGTTA (SEQ ID NO:14). Each reaction contained 2 µl of first strand cDNA and a final concentration of 1 µM sense and antisense primer, 2.5 mM $MgCl_2$, 0.2 mM dNTPs, and 1.25 unit Taq DNA Polymerase (Promega, Madison, Wis.) in 1× buffer (Taq DNA Polymerase 10× Reaction Buffer without $MgCl_2$, Promega, Madison, Wis.). PCR was performed for 45 cycles for the $1^{st}$ round, and 30 cycles for the $2^{nd}$ round with the following setting: heating 2 min 94 C, cycle for 30 sec 94 C, 30 sec 60 C (annealing), and 30 sec 72 C (extension), with a final extension step of 10 min 72 C. Two µl product from the $1^{st}$ round are used in the $2^{nd}$ round using the same overall set-up. Products are analyzed by agarose gel electrophoresis.

Example 14

Use of MNV-1 Infected Mice as Small Animal Model of *Norovirus* Infection

To determine whether T and B cell mediated immunity is required for resistance to MNV-1, wild-type and RAG1−/− mice were infected by the i.c. route and followed for 90 days (data not shown). Surprisingly, MNV-1 infection does not kill RAG1−/− mice (n=20) after direct i.c. inoculation even though these mice are typically highly susceptible to infection with a range of different viruses. The finding that RAG−/− mice are resistant to lethal disease argues that typical adaptive responses are not required for protection from lethal disease. This finding may explain in part contradictory conclusions as to the importance of antibody in resistance to *Norovirus* disease. While B and T cell responses are not required for resistance to lethal infection, it may be that pre-existing immunity influences the pathogenicity of MNV-1. Alternatively, the presence of immune cells may contribute to disease induced by MNV-1 as is seen for lymphocytic choriomeningitis virus.

Together with a course of clinical illness too brief to allow typical adaptive responses, these studies in RAG−/− mice beg the question of whether innate rather than acquired immunity is critical for resistance to calicivirus infection. We therefore inoculated a variety of mouse strains lacking components of the innate immune system with MNV-1. The peroral (p.o.) and intranasal (i.n.) routes were tested in addition to the i.c. route since the physiologic routes of infection for human caliciviruses are oral and respiratory. Mice lacking the IFNαβ receptor or the IFNγ receptor were no more susceptible to lethal infection than wild-type controls (FIG. 5A). In contrast, mice lacking both IFNαβ and IFNγ receptors were more susceptible to lethal infection than congenic controls after either i.c. or i.n. inoculation with MNV-1 (FIG. 5B). These data demonstrate that the IFN receptors can compensate for each other in resistance to MNV-1 infection such that only deficiency in both receptors leads to lethality. Mice deficient in inducible nitric oxide synthetase (iNOS) or in the RNA activated protein kinase PKR, two IFN regulated proteins with antiviral properties, were also resistant to lethal MNV-1 infection after i.c. or p.o. inoculation (FIG. 5A).

Since deficiency in both IFN receptors is required to predispose to lethal MNV-1 infection, we reasoned that a component of the innate immune system that can be activated by either the IFNαβ or the IFNγ receptor was critical for MNV-1 survival. We therefore tested the hypothesis that the latent cytoplasmic transcription factor STAT1, which is shared by both the IFNαβ and IFNγ signaling pathways, was critical for resistance to calicivirus infection. STAT1 deficiency resulted in lethal MNV-1 infection in mice with T and B cells (STAT1−/−, FIG. 5C), mice lacking T and B cells (RAG/STAT, FIG. 5D), and mice lacking PKR (PKR−/−STAT−/−, FIG. 5E) by all routes analyzed. Thus STAT1 is the first host component identified as essential for resistance to lethal *Norovirus* infection, and is required for survival even when T and B cells are present.

Having identified STAT1 as essential for calicivirus resistance, we then investigated the relationship between the interferon receptors and STAT1. No statistically significant differences were found in the survival of IFNαβγR −/− and STAT1−/− mice after either i.c. or i.n. inoculations. However after p.o. inoculation, deficiency of STAT1, but not deficiency in both IFNαβ and IFNγ receptors, led to lethal infection (see FIGS. 5B and C). This might suggest that STAT1 has IFN receptor-independent effects that are critical for *Norovirus* resistance. Supporting this are findings that the biological effects of STAT1 do not completely overlap with those of the IFN receptors during viral infection since there are both STAT1-independent antiviral effects of the IFN receptors, and IFN receptor-independent effects of STAT1.

What is claimed is:

1. A method for determining presence, absence or quantity of MNV-1 in a tissue, organ or feces sample of a mouse, the method comprising:
   a) synthesizing cDNA from RNA comprised by the tissue, organ or feces sample; and
   b) detecting MNV-1 cDNA by a PCR assay if MNV-1 is present in the sample,
   wherein the organ is selected from the group consisting of lung, intestine and brain.

2. A method in accordance with claim 1, wherein the PCR assay is selected from the group consisting of a real time PCR assay and a nested PCR assay.

3. A method in accordance with claim 1, wherein the PCR assay uses at least one sense primer and at least one antisense primer, wherein the sequence of the sense primer is selected from the group consisting of SEQ ID NO:15, SEQ ID NO:17 and SEQ ID NO:19, and the sequence of the antisense primer is selected from the group consisting of SEQ ID NO:16, SEQ ID NO:18 and SEQ ID NO:20.

4. A method in accordance with claim 3, wherein the sequence of the sense primer is set forth as SEQ ID NO:15, and the sequence of the antisense primer is set forth as SEQ ID NO:16.

5. A method in accordance with claim 1, wherein the sequence of the sense primer is set forth as SEQ ID NO:17, and the sequence of the antisense primer is set forth as SEQ ID NO:18.

6. A method in accordance with claim 1, wherein the sequence of the sense primer is set forth as SEQ ID NO:19, and the sequence of the antisense primer is set forth as SEQ ID NO:20.

7. A method in accordance with claim 2, wherein the PCR assay comprises a nested PCR assay, comprising:
   subjecting the cDNA to a first amplification reaction using a first sense primer and a first anti-sense primer; and
   subjecting reaction product of the first amplification reaction to a second amplification reaction using a second sense primer and a second anti-sense primer, wherein the first sense primer and the first anti-sense primer hybridize to target sequences comprised by MNV-1, and the second sense primer and a second anti-sense primer hybridize to target sequences comprised by a reaction product of the first amplification reaction, if MNV-1 is present in the sample.

8. A method in accordance with claim 7, wherein the primers are specific to ORF2 of an MNV-1.

9. A method in accordance with claim 8, wherein the first sense primer comprises the sequence set forth as SEQ ID NO: 15, the first anti-sense primer comprises the sequence set forth as SEQ ID NO: 16, the second sense primer comprises the sequence set forth as SEQ ID NO: 17 and the second anti-sense primer comprises the sequence set forth as SEQ ID NO: 18.

* * * * *

SEQUENCE LISTING

<160> NUMBER OF SEQ ID NOS: 54

<210> SEQ ID NO 1
<211> LENGTH: 7726
<212> TYPE: DNA
<213> ORGANISM: Murine Norovirus type 1
<220> FEATURE:
<221> NAME/KEY: misc_feature
<222> LOCATION: (147)..(5024)
<223> OTHER INFORMATION: ORF1

```
<220> FEATURE:
<221> NAME/KEY: misc_feature
<222> LOCATION: (5057)..(6682)
<223> OTHER INFORMATION: ORF2
<220> FEATURE:
<221> NAME/KEY: misc_feature
<222> LOCATION: (6682)..(7305)
<223> OTHER INFORMATION: ORF3

<400> SEQUENCE: 1
gtgaattcta gaaggcaacg ccatcttctg cgccctctgt gcgcaacaca gagaaacgca      60
aaaacaagaa ggcttcgyct aaagctagtg tctcctttgg agcacctagc cccctctctt     120
cggagagcga agacgaartt aattacatga ccccctcctga gcaggaagct cagcccggcg    180
cccttgcggc ccttcatgcg gaagggccgc ttgccgggct cccgtgacg cgtagtgatg      240 cacgcgtgct gatcttcaat gagtgggagg agaggaagaa gtctgatccg tggctacggc    300
tggacatgtc tgataaggct atcttccgcc gttaccccca tctgcggcct aaggaggata    360
ggcctgacgc gccctcccat gcggaggacg ctatggatgc caaggagcct gtgatcggct    420
ctatcttgga gcaggatgat cacaagtttt accattactc tgtctacatc ggtggcggcc    480
ttgtgatggg ggtcaacaac cccagtgctg cggtctgcca ggcaacgatt gatgtggaga    540
agctacacct ctggtggcgg cctgtctggg agccccgcca wccccttgac tcggctgagt    600
tgaggaagtg cgtgggcatg actgtcccct acgtggccac caccgtcaac tgttatcagg    660
tctgctgctg gattgttggc atcaaggaca cctggctgaa gagggcgaag atctctagag    720
atctgcccct ctacagcccc gtccaggact ggaacgtcga ccccaggag cccttcattc      780 catccaagct caggatggtc tcggatggca tcctggtggc cttgtcggca gtgattggcc    840
ggccaattaa gaacctactg gcctcagtta agccgctcaa cattctcaac atcgtgctga    900
gctgtgattg gacctttcg ggcattgtca atgccctgat cttgcttgct gagctctttg      960
acatcttttg gaccccccct gatgtracca rctggatgat ctctatcttc ggggaatggc    1020
aggccgaagg gccttcgac cytgctcttg acgtggtgcc caccctgttg ggcgggatcg     1080
ggatggcttt tggcctcrcc tctgagacca tcgggcgcaa gctcdcttcc accaactcgg    1140
ctctcaaggc cgcccaagag atgggcaagt cgccataga ggtcttcaag caaattatgg     1200
cctggatctg gccctctgag gacccagtgc cagcccctctt atccaacatg gagcaggcca   1260
tcattaagaa tgagtgtcaa ctdgagaacc aactcacggc catgttgcgg gatcgcaacg    1320
caggggctga attcctvagg tcccttgatg aggaggagca ggaagtccgc aagatcgcag    1380
ctaagtgcgg caactcggcc accactggaa ccaccaacgc tctgctggcc aggatcagca    1440
tggcccgcgc ggcctttgag aaagctcgcg ctgaacagac ctcccgagtc cgccctgtgg    1500
tgdtcatggt ctcaggcagg cccgggatcg ggaaaacctg cttttgccaa aacctagcca    1560
agaggattgc tgcgtccctg ggtgatgaga cctctgttgg catcatacca cgcgctgatg    1620
tcgaccactg ggatgcttac aagggagcca gagtggttct ctgggatgat ttcggcatgg    1680
acaacgtggt gaaggatgca ctgaggcttc agatgcttgc cgacacgtgc ccagtgacac    1740
tcaattgtga caggattgag aacaagggaa agatgyttga ctctcaggtc attatcatca    1800
ccacaaatca acaaacccc gygcccctgg actatgtcaa cctggaggcg gtctgccgcc     1860
gcatagattt cctggtttat gmtgagagcc ctgttgttga tgatgctcgg gccagagccc    1920
ctggcgatgt gaatgcagtg aaagctgcca tgaggcccga ttacagccac atcaatttca    1980
tcttggcacc gcaggcggc tttgaccgtc gggaaacacc ccctacggta agggcgtcac     2040
```

```
caagatcatt ggcgccactg ctctttgcgc gagagcggtt gctcttgtcc atgagcgcca   2100
tgatgatttc ggcctccaga acaaggtcya tgactttgat gcgcgcaarg tcaccgcctt   2160
caaagccatg gcggctgacg ccggcattcc atggtacaaa atggcagcta ttgggtgcaa   2220
agcaatgggg gtgcacctgt gtagaggagg ccatgcattt acttaaggat tatgaggtgg   2280
ctccctgtca ggtgatctac aatggtgcca cctataatgt gagctgcatc aagggtgccc   2340
caatggttga aaaggtcaag gagcctgaat tgcccaaaac acttgtcaac tgtgtcagaa   2400
ggataaagga ggcccgcctc cgctgctact gtaggatggc tgctgacgtc atcacgtcca   2460
ttctgcaggc ggccggcacg gccttctcta tttaccacca gattgagaag aggtctagac   2520 catccttta ttgggatcat ggatacacct accgtgacgg acctggatcc tttgacatct   2580
ttgaggatga cgatgatggg tggtaccact ctgaggaaa aagggcaag aacaagaagg   2640 gccgggggcg acccggagtc ttcagaaccc gtgggctcac ggatgaggag tacgatgaat   2700
tcaagaagcg ccgcgagtct aggggcggca agtactccat tgatgattac ctcgctgrcc   2760
gcgagcgaga agaagaactc ctggagcggg acgaggagga ggctatcttc ggggayggct   2820
tcgggttgaa ggccacccgc cgttcccgca aggcagagag agccaaactg ggcctggttt   2880
ctggtggcga catccgcgcc cgcaagccga tcgactggaa tgtggttggc ccctcctggg   2940
ctgacgatga ccgccaggtc gctacggcga aagatcaac tttgaggccc cagtytccat   3000
ctggtcccgt gttgtgcagt tcggcacggg gtggggcttt tggggtgagc ggccacgtct   3060
tcatcaccgc caagcatgtg gcgccccca agggcacgga gatctttggg cgcaagcccg   3120
gggacttcac tgtcrcttcc agcggggact tcttgaagta ctacttcacc agcgccgtca   3180
ggcctgacrt tccgccatg gtcctggaga atgggtgcca ggaggcgtc gtcgcctcgg   3240 tccttgtcaa gagagcctcc ggcgagatgc ttgccctggc tgtcaggatg ggttcacagg   3300
ccgccatcaa gattggtagt gccgttgtgc atgggcaaac tggcatgctc ctgactggct   3360
ctaatgccaa ggcccaggac ctcgggacca tcccgggcga ctgtggctgt ccctatgttt   3420
ataagaaggg taacacctgg gttgtgattg gggtgcacgt ggcggccact aggtctggta   3480
acacagtcat tgccgccact cacggagaac ccacacttga ggctctggag ttccagggac   3540 ccccatgct tccccgcccc tcaggcacct atgcaggcct ccccatcgcc gattacggcg   3600
acgctccccc cttgagcacc aagaccatgt tctggcgtac ctcgccagag aagcttcccc   3660
ctggggcttg ggagccagcc tatctcggct ctaaagatga gagggtggac ggtccttccc   3720
ttcagcaggt catgcgagat cagcttaagc cctattcaga accacgcggt ctgcttcccc   3780
ctcaagaaat ccttgatgca gtctgcgacg ccattgagaa ccgccttgag aacacccttg   3840
aaccacagaa gccctggaca tttaagaagg cttgtgagag cttggacaag aacaccagya   3900
gygggtatcc ctatcacaag cagaagagca aggactggac ggggagcgct tttattggcg   3960
rtcttggtga ccaggccacc cacgccaaca acatgtgatga gatgggtaaa tccatgcgac   4020
ccatttatac agctgccctc aaggatgaac tggttaagcc agacaagatc tacgggaaga   4080
taaagaagag gcttctctgg ggctctgacc ttgrcaccat gattcgcgct gcccgtgcyt   4140
ttggcccttt ctgtgatgct ctgaaagaar cctgcatttt caaccccatc agagtgggca   4200
tgtcgatgaa cgaagatggc cccttcatct tcgcaagaca cgccaatttc aggtaccaca   4260
tggatgctga ctataccagg tgggactcca cccaacagag agccatccta aagcgcgctg   4320
gygacatcat ggygcgcctc tcccctgagc cagacttggc tcgggttgtc atggatgatc   4380
tcctggcccc ctcgctgttg gacgtcggcg actrtaagat cgttgtcgag gagggggctcc   4440
```

```
catccggctg cccttgcacc acacagctga atagtttggc tcactggatt ttgacccttt    4500
gtgcaatggt tgaggtaacc cgagttgacc ctgacattgt gatgcaagaa tctgagttyt    4560
ccttctatgg tgatgacgag gtggtttcga ccaacctcga gttggatatg gttaagtaca    4620
ccatggcttt gaggcggtac ggtctcctcc cgactcgcgc ggacaaggag gagggacctc    4680
tggagcgtcg ccagacgctg cagggcatct ccttcctgcg ccgtgcgata gttggtgacc    4740
agtttgggtg gtacggtcgt cttgatcgtg ccagcatcga ccgccagctc ctctggacta    4800
aaggacctaa ccaccagaac ccctttgaga ctctccctgg acatgctcag agaccctccc    4860
aactaatggc cctgctcggt gaggctgcca tgcatggtaa aaagtattac aggactgtgg    4920
cttcccgtgt ctccaaggag gccgcccaaa gtgggatara aatggtagtc cccacgccac    4980
cgatctgttt tgcgctgggt gcgctttgga caatgatg ctgagacccc gcaggaacgc    5040
tcagcagtct ttgtgaatga ggatgagtga tggcgcagcg ccaaaagcca atggctctga    5100
ggccagcggc caggatcttg ttcctgccgc cgttgaacag gccgtcccca ytcaacccgt    5160
ggctggcgcg gctcttgccg ccccccgccgc cgggcaaatt aaccaaattg rccctggat    5220 cttccaaaat tttgtccagt gccccttgg tgagttttcc atttcgcctc gaaacacccc    5280
aggtgaaata ctgtttgatt tggccctcgg gccagggctt aaccctacc ttgcccacct    5340 ctcagccatg tacaccggct gggttgggaa crtggaggtt cagctggtcc tcgccggcaa    5400
tgcctttact gctggcaagg tggttgttgc ccttgtacca ccctatttc ccaaggggtc    5460 actcaccact gcccagatca catgcttccc acatgtcatg tgtgatgtgc gcaccctgga    5520
gcccattcaa ctccctcttc ttgatgtgcg tcgagtcctt tggcatgcta cccaggatca    5580
agaggaatct atgcgcctgg tttgcatgct gtacacgcca ctccgcacaa acagcccggg    5640
tgatgagtct tttgtggtct ctggccgcct tctttctaag ccggcggctg atttcaattt    5700
tgtctaccta actccccca tagagagaac catctaccgg atggtcgact tgcccgtgat    5760
acagccgcgg ctgtgcacgc acgcacgttg gcctgccccg gtctatggtc tcttggtgga    5820
cccatccctc ccctcaaatc cccagtggca gaatggaagg gtgcacgttg atgggaccct    5880
gcttggtacc accccaatct ccggttcatg ggtgtcctgc tttgcgkcgg aggctgccta    5940
taagttccaa tcgggcaccg gtgaggtggc gacattcacc ctgattgagc aggatggatc    6000
tgcctacgtc cccggtgaca gggcagcacc actcgggtta ccccgatttc tctgggcaac    6060
tggagatcga ggtccagacc gagaccacca agactggaga caagctcaag gtcaccactt    6120
tgagatgatt cttggcccaa cgaccaacgc ggaccaggcc ccctaccagg gcagggtgtt    6180
cgccagcgtc actgctgcgg cctctcttga cttggtggat ggcagggttc gtgcggtccc    6240
aagatccatc tacggttttc aggacaccat ccctgaatac aacgatgggc tactggttcc    6300
ccttgccccc ccaattggtc cctttctccc cggcgaggtc ctcctgaggt tccggaccta    6360
catgcgtcag atcgacaccg ctgacgccgc agcagaggcg atagactgtg cactccccca    6420
ggagtttgtc tcctggttcg cgtctaacgc gttcaccgtg cagtccgagg ccctgctcct    6480
tagatacagg aacaccctga ctgggcaact gctgttcgag tgcaagctct acaacgaagg    6540
ttacatcgcc ttgtcttatt ccggctcagg acccctcacc ttcccgaccg atggcatctt    6600
tgaggtcgtc agttgggttc ctcgccttta ccaattggcc tctgtgggaa gtttggcaac    6660
aggccgaatg ctcaaacaat aatggctggt gctcttttg gagcgattgg aggtggcctg    6720
atgggcataa ttggcaattc catctcaaat gttcaaaacc ttcaggcaaa caacaattg    6780 gcagctcagc aatttggtta taattcttcc ctgcttgcaa cgcaaattca gcccagaag    6840
```

-continued

```
gatctcactc tgatggggca gcaattcaac cagcagctcc aaaccaactc tttcaagcac      6900
gacttggaaa tgcttggcgc tcaggtgcaa gcccaggcgc aggcccagga gaacgccatc      6960
aatatcaaaa cggcgcagct ccaggccgca ggcttttcaa agacagatgc cacacgcctt      7020
gccttggggc agcagcccac gagggccgtg gattggtctg ggacgcggta ctacaccgct      7080
aaccagccag tcacgggctt ctcgggtggc tttaccccaa cctacactcc aggtaggcaa      7140
gtgacatccc gccctgtgga cacatcccct taccgatct cgggtggacg cttgccctcc       7200
cttcgtggag gttcctggtc cccgcgcgac catacgccgg cgactcaagg cacctacacg      7260
aacggacggt tcgtgtctct ccctaagatc gggagtagca gggcataggt tggaagagaa      7320
accttttgtg aaaatgattt ctgcttactg ctttcttttc tttgtggtag ttagatgcat      7380
ttcgagggcc gtggattggt ctgggacgcg gtactacacc gctaaccagc cagtcacggg      7440
cttctcgggt ggctttaccc caacctacac tccaggtagg caagtgacat cccgccctgt      7500
ggacacatcc cctctaccga tctcgggtgg acgcttgccc tcccttcgtg gaggttcctg      7560
gtccccgcgc gaccatacgc cggcgactca aggcacctac acgaacggac ggttcgtgtc      7620
tctccctaag atcgggagta gcagggcata ggttggaaga gaaaccttt gtgaaaatga       7680 tttctgctta ctgctttctt ttctttgtgg tagttagatg catttc                     7726
```

<210> SEQ ID NO 2
<211> LENGTH: 1625
<212> TYPE: PRT
<213> ORGANISM: Murine Norovirus type 1
<220> FEATURE:
<221> NAME/KEY: misc_feature
<222> LOCATION: (145)..(145)
<223> OTHER INFORMATION: Variable amino acid
<220> FEATURE:
<221> NAME/KEY: misc_feature
<222> LOCATION: (282)..(282)
<223> OTHER INFORMATION: Variable amino acid
<220> FEATURE:
<221> NAME/KEY: misc_feature
<222> LOCATION: (299)..(299)
<223> OTHER INFORMATION: Variable amino acid
<220> FEATURE:
<221> NAME/KEY: misc_feature
<222> LOCATION: (318)..(318)
<223> OTHER INFORMATION: Variable amino acid
<220> FEATURE:
<221> NAME/KEY: misc_feature
<222> LOCATION: (327)..(327)
<223> OTHER INFORMATION: Variable amino acid
<220> FEATURE:
<221> NAME/KEY: misc_feature
<222> LOCATION: (453)..(453)
<223> OTHER INFORMATION: Variable amino acid
<220> FEATURE:
<221> NAME/KEY: misc_feature
<222> LOCATION: (544)..(544)
<223> OTHER INFORMATION: Variable amino acid
<220> FEATURE:
<221> NAME/KEY: misc_feature
<222> LOCATION: (559)..(559)
<223> OTHER INFORMATION: Variable amino acid
<220> FEATURE:
<221> NAME/KEY: misc_feature
<222> LOCATION: (579)..(579)
<223> OTHER INFORMATION: Variable amino acid
<220> FEATURE:
<221> NAME/KEY: misc_feature
<222> LOCATION: (668)..(668)
<223> OTHER INFORMATION: Variable amino acid
<220> FEATURE:
<221> NAME/KEY: misc_feature
<222> LOCATION: (871)..(871)
<223> OTHER INFORMATION: Variable amino acid

```
<220> FEATURE:
<221> NAME/KEY: misc_feature
<222> LOCATION: (950)..(950)
<223> OTHER INFORMATION: Variable amino acid
<220> FEATURE:
<221> NAME/KEY: misc_feature
<222> LOCATION: (997)..(997)
<223> OTHER INFORMATION: Variable amino acid
<220> FEATURE:
<221> NAME/KEY: misc_feature
<222> LOCATION: (1015)..(1015)
<223> OTHER INFORMATION: Variable amino acid
<220> FEATURE:
<221> NAME/KEY: misc_feature
<222> LOCATION: (1272)..(1272)
<223> OTHER INFORMATION: Variable amino acid
<220> FEATURE:
<221> NAME/KEY: misc_feature
<222> LOCATION: (1323)..(1323)
<223> OTHER INFORMATION: Variable amino acid
<220> FEATURE:
<221> NAME/KEY: misc_feature
<222> LOCATION: (1342)..(1342)
<223> OTHER INFORMATION: Variable amino acid
<220> FEATURE:
<221> NAME/KEY: misc_feature
<222> LOCATION: (1396)..(1396)
<223> OTHER INFORMATION: Variable amino acid
<220> FEATURE:
<221> NAME/KEY: misc_feature
<222> LOCATION: (1423)..(1423)
<223> OTHER INFORMATION: Variable amino acid
<220> FEATURE:
<221> NAME/KEY: misc_feature
<222> LOCATION: (1605)..(1605)
<223> OTHER INFORMATION: Variable amino acid

<400> SEQUENCE: 2

Met Thr Pro Pro Glu Gln Glu Ala Gln Pro Gly Ala Leu Ala Ala Leu
 1               5                  10                  15

His Ala Glu Gly Pro Leu Ala Gly Leu Pro Val Thr Arg Ser Asp Ala
            20                  25                  30

Arg Val Leu Ile Phe Asn Glu Trp Glu Arg Lys Lys Ser Asp Pro
        35                  40                  45

Trp Leu Arg Leu Asp Met Ser Asp Lys Ala Ile Phe Arg Arg Tyr Pro
    50                  55                  60

His Leu Arg Pro Lys Glu Asp Arg Pro Asp Ala Pro Ser His Ala Glu
65                  70                  75                  80

Asp Ala Met Asp Ala Lys Glu Pro Val Ile Gly Ser Ile Leu Glu Gln
                85                  90                  95

Asp Asp His Lys Phe Tyr His Tyr Ser Val Tyr Ile Gly Gly Gly Leu
            100                 105                 110

Val Met Gly Val Asn Asn Pro Ser Ala Ala Val Cys Gln Ala Thr Ile
        115                 120                 125

Asp Val Glu Lys Leu His Leu Trp Trp Arg Pro Val Trp Glu Pro Arg
    130                 135                 140

Xaa Pro Leu Asp Ser Ala Glu Leu Arg Lys Cys Val Gly Met Thr Val
145                 150                 155                 160

Pro Tyr Val Ala Thr Thr Val Asn Cys Tyr Gln Val Cys Cys Trp Ile
                165                 170                 175

Val Gly Ile Lys Asp Thr Trp Leu Lys Arg Ala Lys Ile Ser Arg Asp
            180                 185                 190

Leu Pro Phe Tyr Ser Pro Val Gln Asp Trp Asn Val Asp Pro Gln Glu
        195                 200                 205
```

```
Pro Phe Ile Pro Ser Lys Leu Arg Met Val Ser Asp Gly Ile Leu Val
210                 215                 220
Ala Leu Ser Ala Val Ile Gly Arg Pro Ile Lys Asn Leu Leu Ala Ser
225                 230                 235                 240
Val Lys Pro Leu Asn Ile Leu Asn Ile Val Leu Ser Cys Asp Trp Thr
            245                 250                 255
Phe Ser Gly Ile Val Asn Ala Leu Ile Leu Leu Ala Glu Leu Phe Asp
                260                 265                 270
Ile Phe Trp Thr Pro Pro Asp Val Thr Xaa Trp Met Ile Ser Ile Phe
            275                 280                 285
Gly Glu Trp Gln Ala Glu Gly Pro Phe Asp Xaa Ala Leu Asp Val Val
290                 295                 300
Pro Thr Leu Leu Gly Gly Ile Gly Met Ala Phe Gly Leu Xaa Ser Glu
305                 310                 315                 320
Thr Ile Gly Arg Lys Leu Xaa Ser Thr Asn Ser Ala Leu Lys Ala Ala
            325                 330                 335
Gln Glu Met Gly Lys Phe Ala Ile Glu Val Phe Lys Gln Ile Met Ala
                340                 345                 350
Trp Ile Trp Pro Ser Glu Asp Pro Val Pro Ala Leu Leu Ser Asn Met
            355                 360                 365
Glu Gln Ala Ile Ile Lys Asn Glu Cys Gln Leu Glu Asn Gln Leu Thr
370                 375                 380
Ala Met Leu Arg Asp Arg Asn Ala Gly Ala Glu Phe Leu Arg Ser Leu
385                 390                 395                 400
Asp Glu Glu Glu Gln Glu Val Arg Lys Ile Ala Ala Lys Cys Gly Asn
            405                 410                 415
Ser Ala Thr Thr Gly Thr Thr Asn Ala Leu Leu Ala Arg Ile Ser Met
                420                 425                 430
Ala Arg Ala Ala Phe Glu Lys Ala Arg Ala Glu Gln Thr Ser Arg Val
            435                 440                 445
Arg Pro Val Val Xaa Met Val Ser Gly Arg Pro Gly Ile Gly Lys Thr
450                 455                 460
Cys Phe Cys Gln Asn Leu Ala Lys Arg Ile Ala Ala Ser Leu Gly Asp
465                 470                 475                 480
Glu Thr Ser Val Gly Ile Ile Pro Arg Ala Asp Val Asp His Trp Asp
            485                 490                 495
Ala Tyr Lys Gly Ala Arg Val Val Leu Trp Asp Asp Phe Gly Met Asp
                500                 505                 510
Asn Val Val Lys Asp Ala Leu Arg Leu Gln Met Leu Ala Asp Thr Cys
            515                 520                 525
Pro Val Thr Leu Asn Cys Asp Arg Ile Glu Asn Lys Gly Lys Met Xaa
530                 535                 540
Asp Ser Gln Val Ile Ile Thr Thr Asn Gln Gln Thr Pro Xaa Pro
545                 550                 555                 560
Leu Asp Tyr Val Asn Leu Glu Ala Val Cys Arg Arg Ile Asp Phe Leu
            565                 570                 575
Val Tyr Xaa Glu Ser Pro Val Val Asp Asp Ala Arg Ala Arg Ala Pro
                580                 585                 590
Gly Asp Val Asn Ala Val Lys Ala Ala Met Arg Pro Asp Tyr Ser His
            595                 600                 605
Ile Asn Phe Ile Leu Ala Pro Gln Gly Gly Phe Asp Arg Arg Glu Thr
610                 615                 620
```

-continued

Pro Pro Thr Val Arg Ala Ser Pro Arg Ser Leu Ala Pro Leu Leu Phe
625                 630                 635                 640

Ala Arg Glu Arg Leu Leu Leu Ser Met Ser Ala Met Met Ile Ser Ala
            645                 650                 655

Ser Arg Thr Arg Ser Met Thr Leu Met Arg Ala Xaa Ser Pro Pro Ser
        660                 665                 670

Lys Pro Trp Arg Leu Thr Pro Ala Phe His Gly Thr Lys Trp Gln Leu
    675                 680                 685

Leu Gly Ala Lys Gln Trp Gly Cys Thr Cys Val Glu Glu Ala Met His
690                 695                 700

Leu Leu Lys Asp Tyr Glu Val Ala Pro Cys Gln Val Ile Tyr Asn Gly
705                 710                 715                 720

Ala Thr Tyr Asn Val Ser Cys Ile Lys Gly Ala Pro Met Val Glu Lys
                725                 730                 735

Val Lys Glu Pro Glu Leu Pro Lys Thr Leu Val Asn Cys Val Arg Arg
            740                 745                 750

Ile Lys Glu Ala Arg Leu Arg Cys Tyr Cys Arg Met Ala Ala Asp Val
        755                 760                 765

Ile Thr Ser Ile Leu Gln Ala Ala Gly Thr Ala Phe Ser Ile Tyr His
    770                 775                 780

Gln Ile Glu Lys Arg Ser Arg Pro Ser Phe Tyr Trp Asp His Gly Tyr
785                 790                 795                 800

Thr Tyr Arg Asp Gly Pro Gly Ser Phe Asp Ile Phe Glu Asp Asp Asp
                805                 810                 815

Asp Gly Trp Tyr His Ser Glu Gly Lys Gly Lys Asn Lys Lys Gly
            820                 825                 830

Arg Gly Arg Pro Gly Val Phe Arg Thr Arg Gly Leu Thr Asp Glu Glu
        835                 840                 845

Tyr Asp Glu Phe Lys Lys Arg Glu Ser Arg Gly Gly Lys Tyr Ser
    850                 855                 860

Ile Asp Asp Tyr Leu Ala Xaa Arg Glu Arg Glu Glu Leu Leu Glu
865                 870                 875                 880

Arg Asp Glu Glu Glu Ala Ile Phe Gly Asp Gly Phe Gly Leu Lys Ala
                885                 890                 895

Thr Arg Arg Ser Arg Lys Ala Glu Arg Ala Lys Leu Gly Leu Val Ser
            900                 905                 910

Gly Gly Asp Ile Arg Ala Arg Lys Pro Ile Asp Trp Asn Val Val Gly
        915                 920                 925

Pro Ser Trp Ala Asp Asp Arg Gln Val Ala Thr Ala Arg Arg Ser
    930                 935                 940

Thr Leu Arg Pro Gln Xaa Pro Ser Gly Pro Val Leu Cys Ser Ser Ala
945                 950                 955                 960

Arg Gly Gly Ala Phe Gly Val Ser Gly His Val Phe Ile Thr Ala Lys
                965                 970                 975

His Val Ala Pro Pro Lys Gly Thr Glu Ile Phe Gly Arg Lys Pro Gly
            980                 985                 990

Asp Phe Thr Val Xaa Ser Ser Gly Asp Phe Leu Lys Tyr Tyr Phe Thr
        995                 1000                1005

Ser Ala Val Arg Pro Asp Xaa Pro Ala Met Val Leu Glu Asn Gly
    1010                1015                1020

Cys Gln Glu Gly Val Val Ala Ser Val Leu Val Lys Arg Ala Ser
    1025                1030                1035

-continued

| | | | | | | | | | | |
|---|---|---|---|---|---|---|---|---|---|---|
|Gly|Glu|Met|Leu|Ala|Leu|Ala|Val|Arg|Met|Gly|Ser|Gln|Ala|Ala|
| |1040| | | |1045| | | |1050| | | | | |
|Ile|Lys|Ile|Gly|Ser|Ala|Val|Val|His|Gly|Gln|Thr|Gly|Met|Leu|
| |1055| | | |1060| | | |1065| | | | | |
|Leu|Thr|Gly|Ser|Asn|Ala|Lys|Ala|Gln|Asp|Leu|Gly|Thr|Ile|Pro|
| |1070| | | |1075| | | |1080| | | | | |
|Gly|Asp|Cys|Gly|Cys|Pro|Tyr|Val|Tyr|Lys|Lys|Gly|Asn|Thr|Trp|
| |1085| | | |1090| | | |1095| | | | | |
|Val|Val|Ile|Gly|Val|His|Val|Ala|Ala|Thr|Arg|Ser|Gly|Asn|Thr|
| |1100| | | |1105| | | |1110| | | | | |
|Val|Ile|Ala|Ala|Thr|His|Gly|Glu|Pro|Thr|Leu|Glu|Ala|Leu|Glu|
| |1115| | | |1120| | | |1125| | | | | |
|Phe|Gln|Gly|Pro|Pro|Met|Leu|Pro|Arg|Pro|Ser|Gly|Thr|Tyr|Ala|
| |1130| | | |1135| | | |1140| | | | | |
|Gly|Leu|Pro|Ile|Ala|Asp|Tyr|Gly|Asp|Ala|Pro|Pro|Leu|Ser|Thr|
| |1145| | | |1150| | | |1155| | | | | |
|Lys|Thr|Met|Phe|Trp|Arg|Thr|Ser|Pro|Glu|Lys|Leu|Pro|Pro|Gly|
| |1160| | | |1165| | | |1170| | | | | |
|Ala|Trp|Glu|Pro|Ala|Tyr|Leu|Gly|Ser|Lys|Asp|Glu|Arg|Val|Asp|
| |1175| | | |1180| | | |1185| | | | | |
|Gly|Pro|Ser|Leu|Gln|Gln|Val|Met|Arg|Asp|Gln|Leu|Lys|Pro|Tyr|
| |1190| | | |1195| | | |1200| | | | | |
|Ser|Glu|Pro|Arg|Gly|Leu|Leu|Pro|Pro|Gln|Glu|Ile|Leu|Asp|Ala|
| |1205| | | |1210| | | |1215| | | | | |
|Val|Cys|Asp|Ala|Ile|Glu|Asn|Arg|Leu|Glu|Asn|Thr|Leu|Glu|Pro|
| |1220| | | |1225| | | |1230| | | | | |
|Gln|Lys|Pro|Trp|Thr|Phe|Lys|Lys|Ala|Cys|Glu|Ser|Leu|Asp|Lys|
| |1235| | | |1240| | | |1245| | | | | |
|Asn|Thr|Ser|Ser|Gly|Tyr|Pro|Tyr|His|Lys|Gln|Lys|Ser|Lys|Asp|
| |1250| | | |1255| | | |1260| | | | | |
|Trp|Thr|Gly|Ser|Ala|Phe|Ile|Gly|Xaa|Leu|Gly|Asp|Gln|Ala|Thr|
| |1265| | | |1270| | | |1275| | | | | |
|His|Ala|Asn|Asn|Met|Tyr|Glu|Met|Gly|Lys|Ser|Met|Arg|Pro|Ile|
| |1280| | | |1285| | | |1290| | | | | |
|Tyr|Thr|Ala|Ala|Leu|Lys|Asp|Glu|Leu|Val|Lys|Pro|Asp|Lys|Ile|
| |1295| | | |1300| | | |1305| | | | | |
|Tyr|Gly|Lys|Ile|Lys|Lys|Arg|Leu|Leu|Trp|Gly|Ser|Asp|Leu|Xaa|
| |1310| | | |1315| | | |1320| | | | | |
|Thr|Met|Ile|Arg|Ala|Ala|Arg|Ala|Phe|Gly|Pro|Phe|Cys|Asp|Ala|
| |1325| | | |1330| | | |1335| | | | | |
|Leu|Lys|Glu|Xaa|Cys|Ile|Phe|Asn|Pro|Ile|Arg|Val|Gly|Met|Ser|
| |1340| | | |1345| | | |1350| | | | | |
|Met|Asn|Glu|Asp|Gly|Pro|Phe|Ile|Phe|Ala|Arg|His|Ala|Asn|Phe|
| |1355| | | |1360| | | |1365| | | | | |
|Arg|Tyr|His|Met|Asp|Ala|Asp|Tyr|Thr|Arg|Trp|Asp|Ser|Thr|Gln|
| |1370| | | |1375| | | |1380| | | | | |
|Gln|Arg|Ala|Ile|Leu|Lys|Arg|Ala|Gly|Asp|Ile|Met|Xaa|Arg|Leu|
| |1385| | | |1390| | | |1395| | | | | |
|Ser|Pro|Glu|Pro|Asp|Leu|Ala|Arg|Val|Val|Met|Asp|Asp|Leu|Leu|
| |1400| | | |1405| | | |1410| | | | | |
|Ala|Pro|Ser|Leu|Leu|Asp|Val|Gly|Asp|Xaa|Lys|Ile|Val|Val|Glu|
| |1415| | | |1420| | | |1425| | | | | |

-continued

```
Glu Gly Leu Pro Ser Gly Cys Pro Cys Thr Thr Gln Leu Asn Ser
    1430                1435                1440

Leu Ala His Trp Ile Leu Thr Leu Cys Ala Met Val Glu Val Thr
    1445                1450                1455

Arg Val Asp Pro Asp Ile Val Met Gln Glu Ser Glu Phe Ser Phe
    1460                1465                1470

Tyr Gly Asp Asp Glu Val Val Ser Thr Asn Leu Glu Leu Asp Met
    1475                1480                1485

Val Lys Tyr Thr Met Ala Leu Arg Arg Tyr Gly Leu Leu Pro Thr
    1490                1495                1500

Arg Ala Asp Lys Glu Glu Gly Pro Leu Glu Arg Arg Gln Thr Leu
    1505                1510                1515

Gln Gly Ile Ser Phe Leu Arg Arg Ala Ile Val Gly Asp Gln Phe
    1520                1525                1530

Gly Trp Tyr Gly Arg Leu Asp Arg Ala Ser Ile Asp Arg Gln Leu
    1535                1540                1545

Leu Trp Thr Lys Gly Pro Asn His Gln Asn Pro Phe Glu Thr Leu
    1550                1555                1560

Pro Gly His Ala Gln Arg Pro Ser Gln Leu Met Ala Leu Leu Gly
    1565                1570                1575

Glu Ala Ala Met His Gly Glu Lys Tyr Tyr Arg Thr Val Ala Ser
    1580                1585                1590

Arg Val Ser Lys Glu Ala Ala Gln Ser Gly Ile Xaa Met Val Val
    1595                1600                1605

Pro Thr Pro Pro Ile Cys Phe Ala Leu Gly Ala Leu Trp Asn Asn
    1610                1615                1620

Gly Cys
    1625

<210> SEQ ID NO 3
<211> LENGTH: 541
<212> TYPE: PRT
<213> ORGANISM: Murine Norovirus type 1
<220> FEATURE:
<221> NAME/KEY: misc_feature
<222> LOCATION: (32)..(32)
<223> OTHER INFORMATION: Variable amino acid
<220> FEATURE:
<221> NAME/KEY: misc_feature
<222> LOCATION: (52)..(52)
<223> OTHER INFORMATION: Variable amino acid
<220> FEATURE:
<221> NAME/KEY: misc_feature
<222> LOCATION: (106)..(106)
<223> OTHER INFORMATION: Variable amino acid
<220> FEATURE:
<221> NAME/KEY: misc_feature
<222> LOCATION: (291)..(291)
<223> OTHER INFORMATION: Variable amino acid

<400> SEQUENCE: 3

Met Arg Met Ser Asp Gly Ala Ala Pro Lys Ala Asn Gly Ser Glu Ala
1               5                   10                  15

Ser Gly Gln Asp Leu Val Pro Ala Ala Val Glu Gln Ala Val Pro Xaa
                20                  25                  30

Gln Pro Val Ala Gly Ala Ala Leu Ala Ala Pro Ala Ala Gly Gln Ile
            35                  40                  45

Asn Gln Ile Xaa Pro Trp Ile Phe Gln Asn Phe Val Gln Cys Pro Leu
        50                  55                  60
```

-continued

```
Gly Glu Phe Ser Ile Ser Pro Arg Asn Thr Pro Glu Ile Leu Phe
 65                  70                  75                  80

Asp Leu Ala Leu Gly Pro Gly Leu Asn Pro Tyr Leu Ala His Leu Ser
                 85                  90                  95

Ala Met Tyr Thr Gly Trp Val Gly Asn Xaa Glu Val Gln Leu Val Leu
            100                 105                 110

Ala Gly Asn Ala Phe Thr Ala Gly Lys Val Val Ala Leu Val Pro
            115                 120                 125

Pro Tyr Phe Pro Lys Gly Ser Leu Thr Thr Ala Gln Ile Thr Cys Phe
    130                 135                 140

Pro His Val Met Cys Asp Val Arg Thr Leu Glu Pro Ile Gln Leu Pro
145                 150                 155                 160

Leu Leu Asp Val Arg Arg Val Leu Trp His Ala Thr Gln Asp Gln Glu
                165                 170                 175

Glu Ser Met Arg Leu Val Cys Met Leu Tyr Thr Pro Leu Arg Thr Asn
            180                 185                 190

Ser Pro Gly Asp Glu Ser Phe Val Ser Gly Arg Leu Leu Ser Lys
        195                 200                 205

Pro Ala Ala Asp Phe Asn Phe Val Tyr Leu Thr Pro Pro Ile Glu Arg
    210                 215                 220

Thr Ile Tyr Arg Met Val Asp Leu Pro Val Ile Gln Pro Arg Leu Cys
225                 230                 235                 240

Thr His Ala Arg Trp Pro Ala Pro Val Tyr Gly Leu Leu Val Asp Pro
                245                 250                 255

Ser Leu Pro Ser Asn Pro Gln Trp Gln Asn Gly Arg Val His Val Asp
            260                 265                 270

Gly Thr Leu Leu Gly Thr Thr Pro Ile Ser Gly Ser Trp Val Ser Cys
        275                 280                 285

Phe Ala Xaa Glu Ala Ala Tyr Lys Phe Gln Ser Gly Thr Gly Glu Val
    290                 295                 300

Ala Thr Phe Thr Leu Ile Glu Gln Asp Gly Ser Ala Tyr Val Pro Gly
305                 310                 315                 320

Asp Arg Ala Ala Pro Leu Gly Leu Pro Arg Phe Leu Trp Ala Thr Gly
                325                 330                 335

Asp Arg Gly Pro Asp Arg Asp His Gln Asp Trp Arg Gln Ala Gln Gly
            340                 345                 350

His His Phe Glu Met Ile Leu Gly Pro Thr Thr Asn Ala Asp Gln Ala
        355                 360                 365

Pro Tyr Gln Gly Arg Val Phe Ala Ser Val Thr Ala Ala Ala Ser Leu
    370                 375                 380

Asp Leu Val Asp Gly Arg Val Arg Ala Val Pro Arg Ser Ile Tyr Gly
385                 390                 395                 400

Phe Gln Asp Thr Ile Pro Glu Tyr Asn Asp Gly Leu Leu Val Pro Leu
                405                 410                 415

Ala Pro Pro Ile Gly Pro Phe Leu Pro Gly Glu Val Leu Leu Arg Phe
            420                 425                 430

Arg Thr Tyr Met Arg Gln Ile Asp Thr Ala Asp Ala Ala Ala Glu Ala
        435                 440                 445

Ile Asp Cys Ala Leu Pro Gln Glu Phe Val Ser Trp Phe Ala Ser Asn
    450                 455                 460

Ala Phe Thr Val Gln Ser Glu Ala Leu Leu Leu Arg Tyr Arg Asn Thr
465                 470                 475                 480
```

-continued

```
Leu Thr Gly Gln Leu Leu Phe Glu Cys Lys Leu Tyr Asn Glu Gly Tyr
                485                 490                 495

Ile Ala Leu Ser Tyr Ser Gly Ser Gly Pro Leu Thr Phe Pro Thr Asp
            500                 505                 510

Gly Ile Phe Glu Val Val Ser Trp Val Pro Arg Leu Tyr Gln Leu Ala
        515                 520                 525

Ser Val Gly Ser Leu Ala Thr Gly Arg Met Leu Lys Gln
    530                 535                 540

<210> SEQ ID NO 4
<211> LENGTH: 208
<212> TYPE: PRT
<213> ORGANISM: Murine Norovirus type 1

<400> SEQUENCE: 4

Met Ala Gly Ala Leu Phe Gly Ala Ile Gly Gly Leu Met Gly Ile
1               5                  10                  15

Ile Gly Asn Ser Ile Ser Asn Val Gln Asn Leu Gln Ala Asn Lys Gln
            20                  25                  30

Leu Ala Ala Gln Gln Phe Gly Tyr Asn Ser Ser Leu Leu Ala Thr Gln
        35                  40                  45

Ile Gln Ala Gln Lys Asp Leu Thr Leu Met Gly Gln Gln Phe Asn Gln
    50                  55                  60

Gln Leu Gln Thr Asn Ser Phe Lys His Asp Leu Glu Met Leu Gly Ala
65                  70                  75                  80

Gln Val Gln Ala Gln Ala Gln Glu Asn Ala Ile Asn Ile Lys
                85                  90                  95

Thr Ala Gln Leu Gln Ala Ala Gly Phe Ser Lys Thr Asp Ala Thr Arg
            100                 105                 110

Leu Ala Leu Gly Gln Gln Pro Thr Arg Ala Val Asp Trp Ser Gly Thr
        115                 120                 125

Arg Tyr Tyr Thr Ala Asn Gln Pro Val Thr Gly Phe Ser Gly Gly Phe
    130                 135                 140

Thr Pro Thr Tyr Thr Pro Gly Arg Gln Val Thr Ser Arg Pro Val Asp
145                 150                 155                 160

Thr Ser Pro Leu Pro Ile Ser Gly Gly Arg Leu Pro Ser Leu Arg Gly
                165                 170                 175

Gly Ser Trp Ser Pro Arg Asp His Thr Pro Ala Thr Gln Gly Thr Tyr
            180                 185                 190

Thr Asn Gly Arg Phe Val Ser Leu Pro Lys Ile Gly Ser Ser Arg Ala
        195                 200                 205

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
tccaggatga catagtccag gggcg                                    25

<210> SEQ ID NO 6
<211> LENGTH: 25
<212> TYPE: DNA
<213> ORGANISM: Artificial Sequence
<220> FEATURE:
<223> OTHER INFORMATION: Primer
```

```
<400> SEQUENCE: 6
tgggatgatt tcggcatgga caacg                                        25

<210> SEQ ID NO 7
<211> LENGTH: 52
<212> TYPE: DNA
<213> ORGANISM: Artificial Sequence
<220> FEATURE:
<223> OTHER INFORMATION: Primer

<400> SEQUENCE: 7
gtggtgctcg agtgcggccg caagctttat tattgtttga gcattcggcc tg          52

<210> SEQ ID NO 8
<211> LENGTH: 56
<212> TYPE: DNA
<213> ORGANISM: Artificial Sequence
<220> FEATURE:
<223> OTHER INFORMATION: Primer

<400> SEQUENCE: 8
atccgaattc tagatgcacc accaccacca ccacatgagg atgagtgatg gcgcag      56

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
cggaattcgg atgaggatga gtgatggcgc a                                 31

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
tctcgacaag cttttattgt ttgagcattc ggcct                             35

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ccaaaagcca atggctctga                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
agttgaatgg gctccagggt                                              20
```

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ccgccgggca aattaaccaa                                              20

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
aggtgggcaa ggtaggggtt a                                            21

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gcgcagcgcc aaaagccaat                                              20

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gagtcctttg gcatgctacc cagg                                         24

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gccgccgggc aaattaacca                                              20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ggcttaaccc ctaccttgcc ca                                           22

<210> SEQ ID NO 19
<211> LENGTH: 18
<212> TYPE: DNA
<213> ORGANISM: Artificial Sequence
<220> FEATURE:
<223> OTHER INFORMATION: Primer

```
<400> SEQUENCE: 19
cagtgccagc cctcttat                                                   18

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
gtcccttgat gaggagga                                                   18

<210> SEQ ID NO 21
<211> LENGTH: 41
<212> TYPE: DNA
<213> ORGANISM: Murine Norovirus type 1

<400> SEQUENCE: 21
ggaaagatgt ttgactctca ggtcattatc atcaccacaa a                         41

<210> SEQ ID NO 22
<211> LENGTH: 42
<212> TYPE: DNA
<213> ORGANISM: Murine Norovirus type 1

<400> SEQUENCE: 22
ggaaagatgt ttgactctca ggtcattatc atcaccacaa at                        42

<210> SEQ ID NO 23
<211> LENGTH: 54
<212> TYPE: DNA
<213> ORGANISM: Murine Norovirus type 1

<400> SEQUENCE: 23
ggaaagatgt ttgactctca ggtcattatc atcaccacaa atcaacaaac cccc           54

<210> SEQ ID NO 24
<211> LENGTH: 65
<212> TYPE: DNA
<213> ORGANISM: Murine Norovirus type 1
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 24
ggaaagatgt ttgactctca ggtcattatn atnaccacaa atnaacaaac cccgcgccc      60 ctgga                                                                 65

<210> SEQ ID NO 25
<211> LENGTH: 64
<212> TYPE: DNA
<213> ORGANISM: Murine Norovirus type 1
<220> FEATURE:
<221> NAME/KEY: misc_feature
<222> LOCATION: (43)..(43)
<223> OTHER INFORMATION: n is a, c, g, or t
```

```
<400> SEQUENCE: 25
ggaaagatgt tgactctca ggtcattatc atcaccacaa atnaacaaac ccccgcgccc    60
ctgg                                                                64

<210> SEQ ID NO 26
<211> LENGTH: 70
<212> TYPE: DNA
<213> ORGANISM: Murine Norovirus type 1

<400> SEQUENCE: 26
ggaaagatgt tgactctca ggtcattatc atcaccacaa atcaacaaac ccccgcgccc    60
ctggactatg                                                          70

<210> SEQ ID NO 27
<211> LENGTH: 73
<212> TYPE: DNA
<213> ORGANISM: Murine Norovirus type 1
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 27
ggaaagatgc tgactctca ggtcattatc atcaccacaa atnaacaaac ccccgcgccc    60
ctgnnctatg tca                                                      73

<210> SEQ ID NO 28
<211> LENGTH: 77
<212> TYPE: DNA
<213> ORGANISM: Murine Norovirus type 1

<400> SEQUENCE: 28
ggaaagatgt tgactctca ggtcattatc atcaccacaa atcaacaaac ccccgcgccc    60
ctggactatg tcaacct                                                  77

<210> SEQ ID NO 29
<211> LENGTH: 77
<212> TYPE: DNA
<213> ORGANISM: Murine Norovirus type 1

<400> SEQUENCE: 29
ggaaagatgt tgactctca ggtcattatc atcaccacaa atcaacaaac ccccgcgccc    60
ctggactatg tcaacct                                                  77

<210> SEQ ID NO 30
<211> LENGTH: 79
<212> TYPE: DNA
<213> ORGANISM: Murine Norovirus type 1

<400> SEQUENCE: 30
ggaaagatgc tgactctca ggtcattatc atcaccacaa atcaacaaac ccccgcgccc    60
ctggactatg tcaacctgg                                                79

<210> SEQ ID NO 31
<211> LENGTH: 79
<212> TYPE: DNA
<213> ORGANISM: Murine Norovirus type 1
```

```
<400> SEQUENCE: 31
ggaaagatgt tgactctca ggtcattatc atcaccacaa atcaacaaac ccccgcgccc      60
ctggactatg tcaacctgg                                                  79

<210> SEQ ID NO 32
<211> LENGTH: 79
<212> TYPE: DNA
<213> ORGANISM: Murine Norovirus type 1

<400> SEQUENCE: 32
ggaaagatgt tgactctca ggtcattatc atcaccacaa atcaacaaac ccccgcgccc      60
ctggactatg tcaacctgg                                                  79

<210> SEQ ID NO 33
<211> LENGTH: 79
<212> TYPE: DNA
<213> ORGANISM: Murine Norovirus type 1

<400> SEQUENCE: 33
ggaaagatgt tgactctca ggtcattatc atcaccacaa atcaacaaac ccccgcgccc      60
ctggactatg tcaacctgg                                                  79

<210> SEQ ID NO 34
<211> LENGTH: 127
<212> TYPE: DNA
<213> ORGANISM: Murine Norovirus type 1

<400> SEQUENCE: 34
ggaaagatgt tgactctca ggtcattatc atcaccacaa atcaacaaac ccccgtgccc      60
ctggactatg tcaacctgga ggcggtctgc cgccgcatag atttcctggt ttatgctgag    120
agccctg                                                              127

<210> SEQ ID NO 35
<211> LENGTH: 127
<212> TYPE: DNA
<213> ORGANISM: Murine Norovirus type 1

<400> SEQUENCE: 35
ggaaagatgt tgactctca ggtcattatc atcaccacaa atcaacaaac ccccgtgccc      60
ctggactatg tcaacctgga ggcggtctgc cgccgcatag atttcctggt ttatgctgag    120
agccctg                                                              127

<210> SEQ ID NO 36
<211> LENGTH: 127
<212> TYPE: DNA
<213> ORGANISM: Murine Norovirus type 1

<400> SEQUENCE: 36
ggaaagatgt tgactctca ggtcattatc atcaccacaa atcaacaaac ccccgtgccc      60
ctggactatg tcaacctgga ggcggtctgc cgccgcatag atttcctggt ttatgctgag    120
agccctg                                                              127

<210> SEQ ID NO 37
<211> LENGTH: 127
<212> TYPE: DNA
<213> ORGANISM: Murine Norovirus type 1
```

<400> SEQUENCE: 37
ggaaagatgt tgactctca ggtcattatc atcaccacaa atcaacaaac ccccgtgccc      60
ctggactatg tcaacctgga ggcggtctgc cgccgcatag atttcctggt ttatgctgag     120
agccctg                                                              127

<210> SEQ ID NO 38
<211> LENGTH: 127
<212> TYPE: DNA
<213> ORGANISM: Murine Norovirus type 1

<400> SEQUENCE: 38
ggaaagatgt tgactctca ggtcattatc atcaccacaa atcaacaaac ccccgtgccc      60
ctggactatg tcaacctgga ggcggtctgc cgccgcatag atttcctggt ttatgctgag     120
agccctg                                                              127

<210> SEQ ID NO 39
<211> LENGTH: 127
<212> TYPE: DNA
<213> ORGANISM: Murine Norovirus type 1

<400> SEQUENCE: 39
ggaaagatgt tgactctca ggtcattatc atcaccacaa atcaacaaac ccccgtgccc      60
ctggactatg tcaacctgga ggcggtctgc cgccgcatag atttcctggt ttatgatgag     120
agccctg                                                              127

<210> SEQ ID NO 40
<211> LENGTH: 127
<212> TYPE: DNA
<213> ORGANISM: Murine Norovirus type 1

<400> SEQUENCE: 40
ggaaagatgt tgactctca ggtcattatc atcaccacaa atcaacaaac ccccgtgccc      60
ctggactatg tcaacctgga ggcggtctgc cgccgcatag atttcctggt ttatgctgag     120
agccctg                                                              127

<210> SEQ ID NO 41
<211> LENGTH: 127
<212> TYPE: DNA
<213> ORGANISM: Murine Norovirus type 1

<400> SEQUENCE: 41
ggaaagatgt tgactctca ggtcattatc atcaccacaa atcaacaaac ccccgtgccc      60
ctggactatg tcaacctgga ggcggtctgc cgccgcatag atttcctggt ttatgctgag     120
agccctg                                                              127

<210> SEQ ID NO 42
<211> LENGTH: 127
<212> TYPE: DNA
<213> ORGANISM: Murine Norovirus type 1

<400> SEQUENCE: 42
ggaaagatgt tgactctca ggtcattatc atcaccacaa atcaacaaac ccccgtgccc      60
ctggactatg tcaacctgga ggcggtctgc cgccgcatag atttcctggt ttatgctgag     120
agccctg                                                              127

<210> SEQ ID NO 43
<211> LENGTH: 127
<212> TYPE: DNA
<213> ORGANISM: Murine Norovirus type 1

<400> SEQUENCE: 43

```
ggaaagatgt tgactctca ggtcattatc atcaccacaa atcaacaaac ccccgtgccc      60
ctggactatg tcaacctgga ggcggtctgc cgccgcatag atttcctggt ttatgctgag     120
agccctg                                                              127
```

<210> SEQ ID NO 44
<211> LENGTH: 127
<212> TYPE: DNA
<213> ORGANISM: Murine Norovirus type 1
<220> FEATURE:
<221> NAME/KEY: misc_feature
<222> LOCATION: (24)..(24)
<223> OTHER INFORMATION: n is a, c, g, or t

<400> SEQUENCE: 44

```
ggaaagatgt tgactctca ggtnattatc atcaccacaa atcaacaaac ccccgtgccc      60
ctggactatg tcaacctgga ggcggtctgc cgccgcatag atttcctggt ttatgctgag     120
agccctg                                                              127
```

<210> SEQ ID NO 45
<211> LENGTH: 127
<212> TYPE: DNA
<213> ORGANISM: Murine Norovirus type 1

<400> SEQUENCE: 45

```
ggaaagatgt tgactctca ggtcattatc atcaccacaa atcaacaaac ccccgtgccc      60
ctggactatg tcaacctgga ggcggtctgc cgccgcatag atttcctggt ttatgatgag     120
agccctg                                                              127
```

<210> SEQ ID NO 46
<211> LENGTH: 117
<212> TYPE: DNA
<213> ORGANISM: Murine Norovirus type 1
<220> FEATURE:
<221> NAME/KEY: misc_feature
<222> LOCATION: (73)..(73)
<223> OTHER INFORMATION: n is a, c, g, or t

<400> SEQUENCE: 46

```
ggaaagatgc tgactctca ggtcattatc ataccacaaa tcaacaaacc ccgcgccct       60 ggactatgtc aanctggagg cggtctgccg ccgcatagat ttcctggttt atgctga       117
```

<210> SEQ ID NO 47
<211> LENGTH: 124
<212> TYPE: DNA
<213> ORGANISM: Murine Norovirus type 1
<220> FEATURE:
<221> NAME/KEY: misc_feature
<222> LOCATION: (75)..(75)
<223> OTHER INFORMATION: n is a, c, g, or t

<400> SEQUENCE: 47

```
ggaaagatgt tgactctca ggtcattatc atcaccacaa atcaacaaac ccccgcgccc      60
ctggactatg tcaanctgga ggcggtctgc cgccgcatag atttcgttta tgatgagagc    120
cctg                                                                 124
```

<210> SEQ ID NO 48
<211> LENGTH: 119
<212> TYPE: DNA
<213> ORGANISM: Murine Norovirus type 1
<220> FEATURE:
<221> NAME/KEY: misc_feature
<222> LOCATION: (75)..(75)
<223> OTHER INFORMATION: n is a, c, g, or t

<400> SEQUENCE: 48
ggaaagatgt ttgactctca ggtcattatc atcaccacaa atcaacaaac ccccgcgccc      60
ctggactatg tcaanctgga ggcggtctgc cgccgcatag atttcctggt ttatgctga     119

<210> SEQ ID NO 49
<211> LENGTH: 127
<212> TYPE: DNA
<213> ORGANISM: Artificial Sequence
<220> FEATURE:
<223> OTHER INFORMATION: Consensus sequence

<400> SEQUENCE: 49
ggaaagatgy ttgactctca ggtcattatc atcaccacaa atcaacaaac ccccgygccc      60
ctggactatg tcaacctgga ggcggtctgc cgccgcatag atttcctggt ttatgmtgag     120
agccctg                                                              127

<210> SEQ ID NO 50
<211> LENGTH: 8
<212> TYPE: PRT
<213> ORGANISM: Artificial Sequence
<220> FEATURE:
<223> OTHER INFORMATION: Illustrative MNV-1 ORF1 motif
<220> FEATURE:
<221> NAME/KEY: misc_feature
<222> LOCATION: (2)..(3)
<223> OTHER INFORMATION: Variable amino acid
<220> FEATURE:
<221> NAME/KEY: misc_feature
<222> LOCATION: (5)..(5)
<223> OTHER INFORMATION: Variable amino acid

<400> SEQUENCE: 50

Gly Xaa Xaa Gly Xaa Gly Lys Thr
1               5

<210> SEQ ID NO 51
<211> LENGTH: 4
<212> TYPE: PRT
<213> ORGANISM: Artificial Sequence
<220> FEATURE:
<223> OTHER INFORMATION: Illustrative MNV-1 ORF1 motif

<400> SEQUENCE: 51

Gly Asp Cys Gly
1

<210> SEQ ID NO 52
<211> LENGTH: 4
<212> TYPE: PRT
<213> ORGANISM: Artificial Sequence
<220> FEATURE:
<223> OTHER INFORMATION: Illustrative MNV-1 ORF1 motif

<400> SEQUENCE: 52

Lys Asp Glu Leu
1

```
-continued

<210> SEQ ID NO 53
<211> LENGTH: 4
<212> TYPE: PRT
<213> ORGANISM: Artificial Sequence
<220> FEATURE:
<223> OTHER INFORMATION: Illustrative MNV-1 ORF1 motif

<400> SEQUENCE: 53

Gly Leu Pro Ser
1

<210> SEQ ID NO 54
<211> LENGTH: 4
<212> TYPE: PRT
<213> ORGANISM: Artificial Sequence
<220> FEATURE:
<223> OTHER INFORMATION: Illustrative MNV-1 ORF1 motif

<400> SEQUENCE: 54

Tyr Gly Asp Asp
1
```